United States Patent
Thomas et al.

(10) Patent No.: US 9,861,524 B2
(45) Date of Patent: Jan. 9, 2018

(54) SMART SHUNT DEVICES AND METHODS

(71) Applicant: NEW JERSEY INSTITUTE OF TECHNOLOGY, Newark, NJ (US)

(72) Inventors: Gordon Albert Thomas, Princeton, NJ (US); Reginald Conway Farrow, Somerset, NJ (US); Alokik Kanwal, Princeton, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 972 days.

(21) Appl. No.: 14/213,170

(22) Filed: Mar. 14, 2014

(65) Prior Publication Data

US 2014/0309577 A1  Oct. 16, 2014

Related U.S. Application Data

(60) Provisional application No. 61/781,606, filed on Mar. 14, 2013.

(51) Int. Cl.
| | |
|---|---|
| *G01L 9/12* | (2006.01) |
| *A61F 9/007* | (2006.01) |
| *G01L 9/00* | (2006.01) |
| *G01F 1/64* | (2006.01) |
| *A61M 27/00* | (2006.01) |

(52) U.S. Cl.
CPC ............ *A61F 9/00781* (2013.01); *G01F 1/64* (2013.01); *G01L 9/007* (2013.01); *G01L 9/0072* (2013.01); *G01L 9/0073* (2013.01); *A61M 27/006* (2013.01); *A61M 2205/0244* (2013.01); *A61M 2205/3327* (2013.01); *A61M 2205/3344* (2013.01)

(58) Field of Classification Search
None
See application file for complete search history.

(56) References Cited

U.S. PATENT DOCUMENTS

| | | | | |
|---|---|---|---|---|
| 4,876,892 A | * | 10/1989 | Arabia | G01L 9/125 331/65 |
| 5,317,917 A | * | 6/1994 | Dufour | G01L 9/0022 73/702 |

(Continued)

OTHER PUBLICATIONS

Di Rocco, C., L. Massimi, and G. Tamburrini, Shunts vs endoscopic third ventriculostomy in infants: are there different types and/or rates of complications? A review. Childs Nerv Syst 22:1573-1589 (2006).

(Continued)

*Primary Examiner* — Andre Allen
(74) *Attorney, Agent, or Firm* — Timothy X. Gibson, Esq.; Gibson & Dernier LLP

(57) ABSTRACT

Devices and methods for the measurement and control of fluid using one or two capacitors are described. The devices use Micro-Electro-Mechanical-Systems (MEMS) and radio-frequency inductive coupling to sense the properties of a fluid in a tube. The single and double capacitor devices may be coupled to shunts implantable in a patient and operable to be interrogated non-invasively. The shunts employing the novel capacitor devices are insensitive to stray signals such as the orientation of a patient's head. The devices are operable to employ a wireless external spectrometer to measure passive subcutaneous components.

15 Claims, 26 Drawing Sheets

(56) References Cited

U.S. PATENT DOCUMENTS

| | | | | |
|---|---|---|---|---|
| 5,417,115 | A | * | 5/1995 | Burns .................... G01L 1/183 331/156 |
| 6,532,834 | B1 | * | 3/2003 | Pinto .................... G01L 9/0072 361/283.3 |
| 2001/0047689 | A1 | * | 12/2001 | McIntosh ............. B81B 3/0086 73/514.32 |
| 2003/0230145 | A1 | * | 12/2003 | Pinto .................... G01L 9/0072 73/718 |
| 2005/0229710 | A1 | * | 10/2005 | O'Dowd .............. G01L 9/0072 73/718 |
| 2012/0272518 | A1 | * | 11/2012 | Cui ........................ G01L 1/142 29/825 |

OTHER PUBLICATIONS

Garton, H.J. and J.H. Platt, Jr., Hydrocephalus. Pediatr Clin North Am, 51(2): p. 305-325 (2004).

Robertson, J.S., M.I. Maraqa, and B. Jennett, Ventriculoperitoneal shunting for hydrocephalus.British Medical Journal, 2(5861): p. 289-292, (1973).

Vinchon, M., et al., Shunt revision for asymptomatic failure: surgical and clinical results. Neurosurgery, 52(2): p. 347-356 (2003).

Caldarelli, M., C. Di Rocco, and F. La Marca, Shunt complications in the first postoperative year in children with meningomyelocele. Childs Nery Syst, 12(12): p. 748-754 (1996).

Blount, J.P., J.A. Campbell, and S.J. Haines, Complications in ventricular cerebrospinal fluid shunting. Neurosurg Clin N Am, 4(4): p. 633-656 (1993).

Kulkarni, A.V. et al., Predicting who will benefit from endoscopic third ventriculostomy compared with shunt insertion in childhood hydrocephalus using the ETV Success Score. J. Neurosurg Pediatrics, . 6(4): p. 310-315 (2010).

Kulkarni, A.V., et al., Endoscopic Third Ventriculostomy Vs Cerebrospinal Fluid Shunt in the Treatment of Hydrocephalus in Children: A Propensity Score-Adjusted Analysis. Neurosurgery, 67(3): p. 588-593 10.1227/01.NEU.0000373199.79462.21 (2010).

Sekula, R.F., et al., Laparoscopically assisted peritoneal shunt insertion for hydrocephalus. British Journal of Neurosurgery, 23(4): p. 439-442 (2009).

Winston, K.R., J.A. Lopez, and J. Freeman, CSF Shunt Failure with Stable Normal Ventricular Size. Pediatric Neurosurgery, 42(3): p. 151-155 (2006).

Akar, O., et al., A wireless batch sealed absolute capacitive pressure sensor. Sensors and Actuators A: Physical, 95 (1): p. 29-38 (2001).

Chang, S.-P. and M.G. Allen, Demonstration for integrating capacitive pressure sensors with read-out circuitry on stainless steel substrate. Sensors and Actuators A, 116(2): p. 195-204 (2004).

Lei, K.F., K.-F. Lee, and M.-Y. Lee, Development of a flexible PDMS capacitive pressure sensor for plantar pressure measurement. Microelectronic Engineering, 99: p. 1-5 (2012).

Ha, D. et al. Polymer-based miniature flexible capacitive pressure sensor for intraocular pressure (IOP) monitoring inside a mouse eye. Biomedical Microdevices, 14(1): p. 207-215 (2012).

Sutera, S.P. and R. Skalak, The History of Poiseuille's Law. Annual Review of Fluid Mechanics, 25: p. 1-20. (1993).

Oosterbroek, R.E., et al., A micromachined pressure/flow-sensor. Sensors and Actuators A: 77: p. 167-177 (1999).

Oosterbroek, R.E., et al. Designing, realization and characterization of a novel capacitive pressure/flow sensor. 1997 International Conference on Solid State Sensors and Actuators, 1997. 0/7803-3829-4/97. Transducers '97 Chicago., pp. 151-154 (1997).

Vlassak, J.J. and W.D. Nix, New bulge test technique for the determination of Young's modulus and Poisson's ratio of thin films. Journal of Materials Research, 7(12): p. 3242-3249 (1992).

Pan, J.Y., et al., Verification of FEM analysis of load-deflection methods for measuring mechanical properties of thin films. in Solid-State Sensor and Actuator Workshop, 1990. CH2783-0/90/ 0000-0070. 4th Technical Digest., IEEE. (1990).

Ohta, T., et al., Development of a Fully Implantable Epidural Pressure (EDP) Sensor, in Intracranial Pressure VII, J. Hoff and A.L. Betz, Editors. Springer-Verlag Berlin Heidelberg. p. 48-51. (Reprinted with permission from Springer Science and Business Media) (1989).

Irani, D.N., Properties and Composition of Normal Cerebrospinal Fluid, in Cerebrospinal Fluid in Clinical Practice, Chapter 10, Editor David N. Irani, Saunders Elsevier, Philadelphia. p. 69-89 (2009).

* cited by examiner

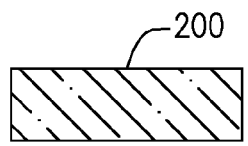
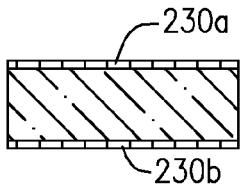
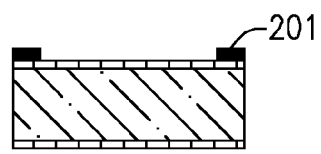
FIG. 17a      FIG. 17b      FIG. 17c
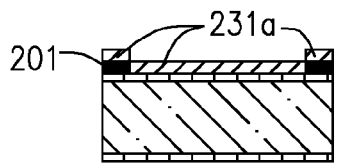
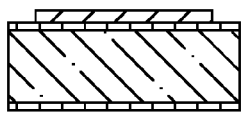
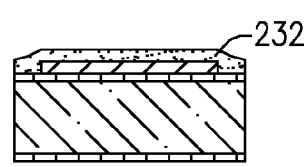
FIG. 17d      FIG.17e      FIG.17f
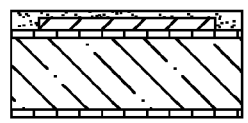
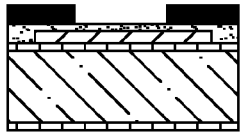
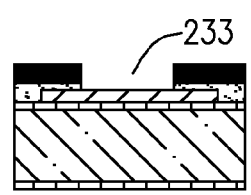
FIG. 17g      FIG 17h      FIG. 17i
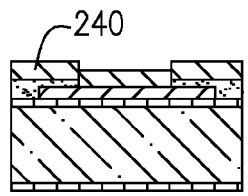
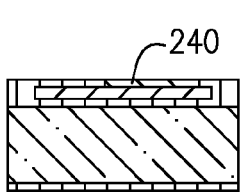
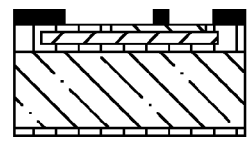
FIG. 17j      FIG. 17k      FIG. 17l

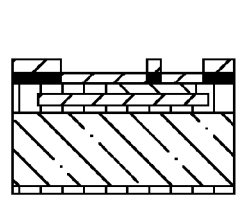 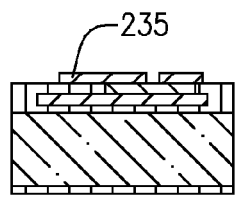 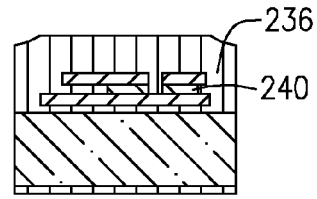
FIG. 17m    FIG. 17n    FIG. 17o
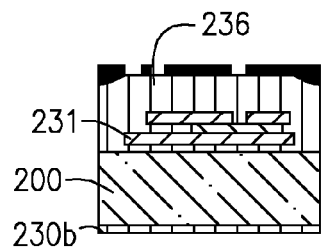 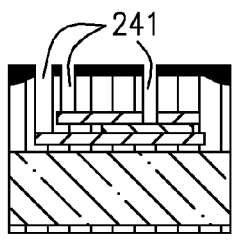 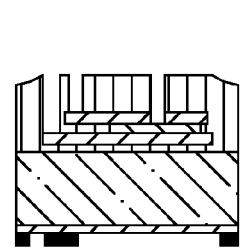
FIG. 17p    FIG. 17q    FIG. 17r
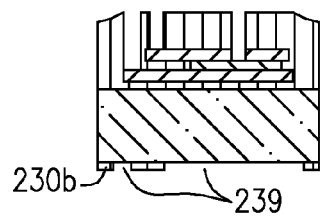 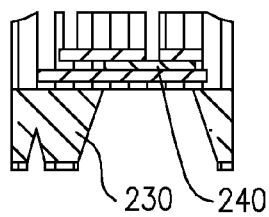 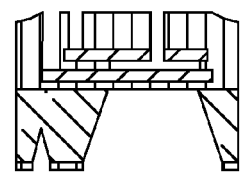
FIG. 17s    FIG. 17t    FIG. 17u

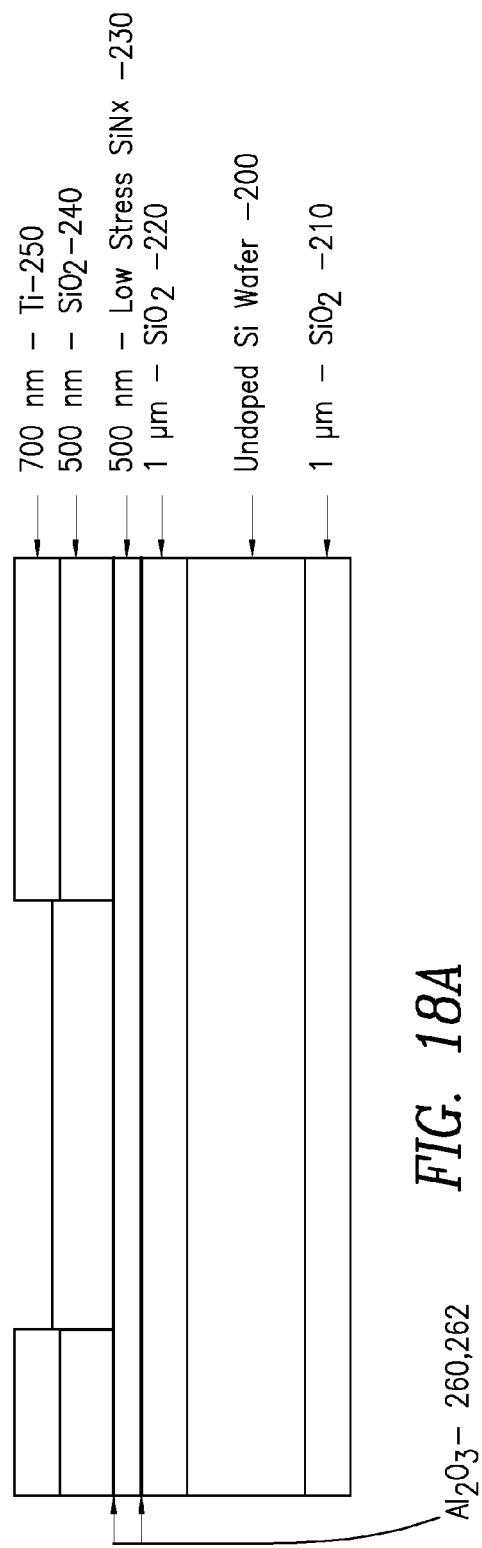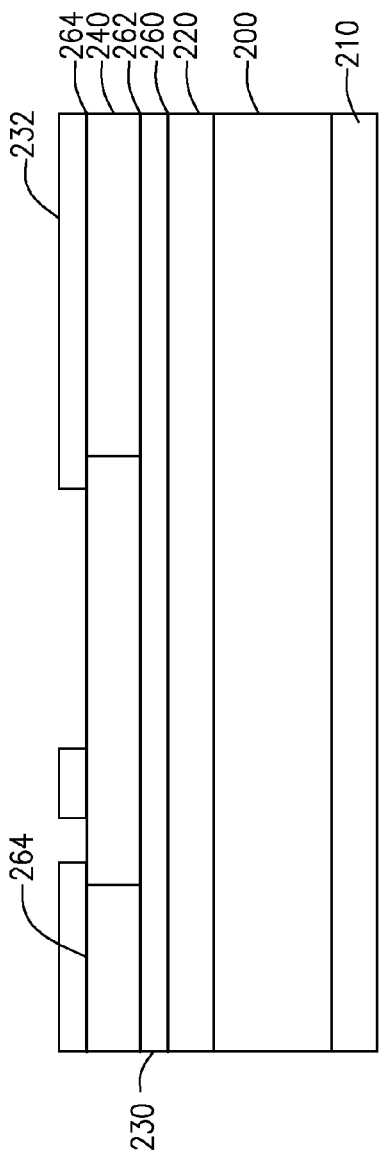
FIG. 18A
FIG. 18B

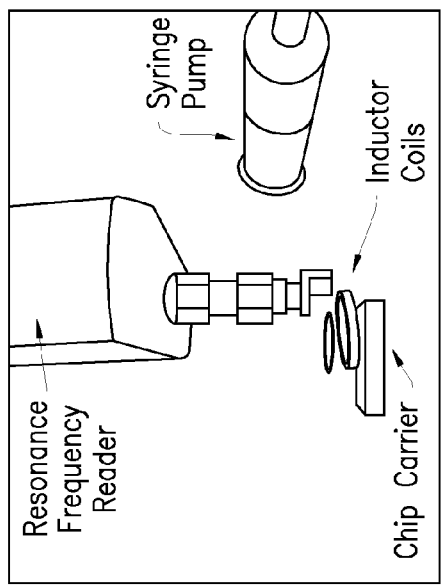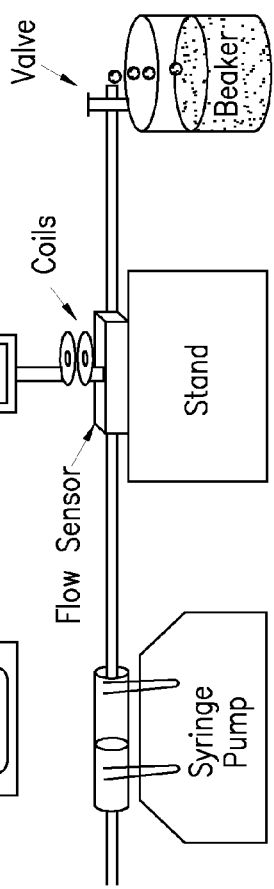
FIG. 20A
FIG. 20B
FIG. 20C

SMART SHUNT DEVICES AND METHODS

CROSS-REFERENCE TO RELATED APPLICATIONS

This application claims the benefit of U.S. Provisional Patent Application No. 61/781,606 filed Mar. 14, 2013, the entirety of which is incorporated herein by reference.

STATEMENT REGARDING FEDERALLY SPONSORED RESEARCH

The research leading to the present invention was supported in part by grants from the National Institutes of Health (NIH 1479-S002 and NINDS R43NS056628-01A2). The United States Government has certain rights in the invention.

FIELD OF THE INVENTION

The invention relates to smart shunts and methods of making and using same.

BACKGROUND

There are applications where there is a need for measuring the properties of a fluid in a tube of a shunt when the orientation and background pressure of the device cannot be accurately controlled, such as in the human body. Examples include the intracranial fluid (in the human brain) and the intraocular fluid (in the human eye). There are medically important features in both cases. For example, the flow rate for intracranial fluid is normally a slow 20 milliliters per hour, but its variation has clinical consequences. Shunts redirect this flow when the associated intracranial pressure becomes abnormally large and is characterized as the disease hydrocephalus. If the flow rate is partially interrupted, such as by an occlusion, the pressure can rise and the resulting rise in pressure can cause neurological damage.

SUMMARY OF THE INVENTION

It would be particularly advantageous for doctors to know about the composition, flow and pressure characteristics of the fluid to understand clinical dangers facing a patient. For example, it would be valuable to know if the flow is decreasing in a way that indicates that an occlusion is beginning to form. Patients would benefit from a therapy that cleared out the shunt tube to restore fluid flow without an operation. Patients and doctors would benefit from information that would allow timely scheduling of surgery to repair a shunt and also from information that would indicate that surgery is unnecessary. Patients and doctors would benefit from a shunt control valve which automatically adjusts to conditions in the tube. Patients and doctors would benefit from the availability of information about the patient at locations remote from the doctors' offices.

Accordingly, there is a need for devices to measure and control varying flow rates and pressures with the needed sensitivity and reliability. There is a particular need for a smart shunt that would improve flow of the cerebrospinal fluid through the brain, which shunt includes a flow meter to signal an alert when the fluid flow rate is too low and control the flow when the rate is too high. There is also a need for a dual capacitor shunt that measures separate pressure and flow adequately.

In accordance with one aspect of the present disclosure, smart shunts employing a differential membrane single-capacitor Micro-Electro-Mechanical-Systems (MEMS) flow meter with a fluid medium are provided which solves problems of inadequate stability and sensitivity. MEMS and radio-frequency inductive coupling may be employed to sense the properties of the fluid in a tube. This uni-capacitor smart shunt has various applications including, but not limited to, medical shunts for the treatment of hydrocephalus, head injury, glaucoma and heart disease. In the biomedical applications the smart shunt may be implanted in a patient and interrogated non-invasively and be insensitive to stray signals such as the orientation of a patient's head. The components of the device include one or more of the following features: flow sensor; pressure sensor; fluid composition sensor; flow enhancer; flow regulator; and communications means. The flow sensors, pressure sensors, fluid composition sensors and flow enhancers disclosed herein use the deformation of a MEMS flexible capacitor plate as a means of converting fluid information into a change in the resonant absorption of a capacitor-inductor loop or the reverse, namely that the absorption of external power can affect the fluid. An external circuit induces an alternating current in the loop and measures the absorption resonance. The regulator is a valve that will respond to the information from the flow sensor, pressure sensor, fluid composition sensor and/or flow enhancer and is operable to adjust the flow rate. The communication means conveys the information about the fluid properties from one of the external components to a doctor or other caregiver.

Prior art flow meters which employ two sensors lack sufficient stability in some applications where the flow is slow or lack sufficient range of the parameters that they can measure. External sources of variation include gravitational and temperature differences between the separate sensors. The single sensor embodiment in the presently disclosed flow meter solves these problems. The differential membrane single-capacitor flow meter disclosed herein eliminates the stability problem because there is a negligible hydrostatic pressure difference between the two sides of the membrane. The flexible membrane responds only to the drop in pressure from the flow, F, when the fluid passes the plate first, P1, then loops back and passes again at P2 after a calibrated flow resistance $R:P1-P2=R*F$. The capacitor forms part of a resonant circuit that can be implanted and requires no internal power, so it can remain in place for decades, in principle. An external reader couples inductively to the internal circuit and can measure very small shifts in the resonant circuit corresponding to small changes in flow. The uni-capacitor devices disclosed herein can measure very small flows. The devices can measure flow continuously and therefore can make dynamic measurements of bodily functions such as pulsatility (oscillations) in the flow of fluid in the brain (cerebrospinal fluid) or the eye (intra-ocular fluid). The presently disclosed devices provide flow readings that are insensitive to the orientation of the patient's position, i.e., lying, standing or sitting.

Many prior art flow meters are not as sensitive as the presently disclosed devices so cannot be used for hydrocephalus or glaucoma. Such prior art flow meters also do not employ an oil medium to transmit the pressure through the space between capacitor plates. This use of oil is unique and is important because the body fluids are conductive (because of salts) and would make the capacitor ineffective if introduced between the capacitor plates. We also have an embodiment that achieves the desired specifications without oil.

The presently disclosed uni-capacitor devices satisfy the medical device requirement of the International Standards Organization (ISO) that a device should survive immersion under two meters of water. Prior art dual capacitor devices would not satisfy ISO requirements because each of the sensitive membranes would be pinned to the fixed capacitor plate, potentially permanently, by a large or very small background pressure. The uni-capacitor devices disclosed herein satisfy ISO requirements. The subject device is more sensitive than prior art dual capacitor devices because the capacitor gap and the flexible plate thickness can be decreased without fear of collapse at normal ambient pressures. The design also permits one to raise the Q of the resonance.

In accordance with a further embodiment a uni-capacitor smart shunt system includes a tube through which the fluid can flow, a sensor that indicates the flow, a meter that measures the sensor, a signal output from the meter that controls a valve in the tube to reduce flow that is too high and a signal output from the meter that produces an alert if the flow is low to an unhealthy extent. The meter may also keep an electronic record. As noted above the differential capacitor design solves problems presented in applications such as shunts.

In accordance with a further aspect the systems may employ wireless information transfer. In one embodiment devices in accordance with the present disclosure are operable to reduce stray signals that obscure the measurement of flow by a factor of over 100.

In accordance with one embodiment a method is provided which includes implanting in a patient a smart shunt with the capability of measuring pressure and flow rate in the shunt as a function of time. The patient is typically one with hydrocephalus or other brain injury that leads to an unhealthy condition of fluid pressure and flow in the cerebrospinal fluid system. A study is made of the patient's cerebrospinal fluid flow, pressure or both as a function of time under controlled conditions to serve as a control. A treatment is administered to the patient. This treatment may consist of drugs, change in eating or drinking, change in activity or other factor that is believed to benefit the patient's condition. A study is made of the patient's cerebrospinal fluid flow, pressure or both as a function of time under the same controlled conditions as in the control measurement. The length of time is long enough to allow the treatment to take effect, which may be less than an hour for some ingested substances and may be longer than several months for some changes in activity. The cerebrospinal fluid flow, pressure or both as a function of time is compared for the test with the control. The test is repeated to determine the reproducibility of the results. The results may be made available for utilization. The methods herein are intended to evaluate both beneficial and deleterious effects. Deleterious effects may include the treatments listed as examples above, but also include other uncontrolled (but potentially controllable) effects such as occlusion of the shunt, and controllable effects such as forces on the patient due to gravity and acceleration.

In one embodiment a method of testing a shunt itself is disclosed for evaluating the precursive behavior to occlusion of the shunt to improve decisions on shunt revision. See, Published U.S. Patent Application 2010/0228179 "No Clog Shunt Using a Compact Fluid Drag Path", the entirety of which is incorporated herein by reference. The method can be used in a brief examination of the shunt in the operating room after the ventricular end is inserted in the head. Occlusion can be detected very quickly by testing the flow of cerebrospinal fluid.

In yet a further embodiment, dual-capacitor smart shunts are provided which are operable to measure both intracranial pressure and shunt flow, and separate pressure and flow adequately. Resonant-frequency, wireless flow sensors may be used to enhance the functionality of ventriculo-peritoneal shunts. Systems in accordance with one or more embodiments employ a pair of capacitors with flexible membranes used as fluid pressure sensors that are in line with the flow. The flow rate through a path with known flow resistance is calculated from the difference in pressure. Wiring inductors to the capacitive sensors forms resonant circuits. Such devices are designed for subcutaneous implantation in the line of flow of the shunt.

Prior art sensors are limited in the range of flow rates that they can measure. The smart shunt system sensors are capable of measuring the flow characteristic of the cerebrospinal fluid in the range from less than 4 mL/hour to above 100 mL/hour. These sensors are suitable for long-term implantation because they use a wireless external spectrometer to measure passive subcutaneous components. The sensors are pressure-sensitive capacitors, with one embodiment in the range of 5 pF with an air gap at atmospheric pressure. Each capacitor is in series with an inductor to provide a resonant frequency that varies with flow rate. In one embodiment, in a constant flow condition, the system is reproducible to <0.3 mL/hr over a month. At variable flow rate, $\dot{V}$, the system can be calibrated reliably and in one embodiment, $\dot{V}$ the resonant frequency, $f_0$, which is in the 200-400 MHz range, follows a second order polynomial with respect to $\dot{V}$. For this sensor system the uncertainty in measuring $f_0$ is 30 kHz which corresponds to a sensitivity in measuring flow of $\Delta\dot{V}=?=0.6$ mL/hr. Pressures up to 20 cm $H_2O$ relative to ambient pressure can also be measured. An implantable twin capacitor system is provided that can measure flow, which is calibrated for the clinically relevant range of hydrostatic pressures. For twin capacitors placed face to face, the properties of a single capacitor are also achieved.

For twin capacitors, placed side by side, other sources of systematic variation within clinical range, such as temperature and ambient pressure, may be smaller than the sensitivity of the system. Accordingly, in a further embodiment a calibration method is provided to maintain clinically useful accuracy over long periods.

In a clinical configuration of systems disclosed herein the dual capacitor sensor may be added to a standard, ventricular-peritoneal shunt with a pressure control valve. A tilt-sensor may also be employed to improve accuracy. In one embodiment a method for obtaining pressure and flow information using twin sensors and a patient's position is provided. The flow originates in the ventricle, goes through a tube to the first sensor, then the second sensor, then a pressure control valve and finally to the peritoneal cavity. Using the system and two patient positions, the set of measurements can determine both the ventricle pressure and the flow. The accuracy is sufficient to make the data clinically useful. With the shunt horizontal, the pressure, P, is determined by the absolute value of either of the pressure sensors, corrected by the hydrostatic pressure calculated from the height, h. When the shunt is vertical, the differential pressure dPf determines the flow, V. For the supine patient position, all of the pressure control valves cut off the flow when the patient is supine in order to prevent back flow. In this condition, the difference pressure between the sensors can be calibrated because the flow is 0. The pressure measured by the implanted sensors is indicative of the pressure in the brain, assuming the end of the shunt tube in the ventricle is horizontal with the sensor. For the vertical patient position, all of the valves are open at some value of pressure when the patient is vertical. The valves restrict the flow to avoid draining the ventricle. In this position, the sensors show an internal hydrostatic offset which is significant, but known, so that the flow can be calculated from any extra frequency shift. A relatively large pressure will be measured at a value due to intracranial pressure plus the hydrostatic pressure between the (known) height of the ventricular end of the shunt tube and the sensor.

One of the most important conditions of the shunt is a malfunction because of an occlusion. Although it may be possible to gain some information from the pressure measurements, the combination of pressure and flow will be most valuable. For example, with a vertical patient, a history of flow readings may be recorded over time. A systematic decrease in the flow rate for a vertical patient, may indicate a narrowing of the flow path between the ventricle and any point in the shunt tube. A stoppage of flow indicates an occlusion. In this case, the pressure will only be due to the height difference in the shunt tube. Further confirmation is that, with the patient horizontal, the ventricular pressure will drop out of the sensor pressure reading.

Devices and methods in accordance with the present disclosure are operable to head off brain injury and death, reduce brain surgeries and test medicines.

BRIEF DESCRIPTION OF THE DRAWINGS

For the purposes of illustration, there are forms shown in the drawings that are presently preferred, it being understood, however, that the invention is not limited to the precise arrangements and instrumentalities shown.

FIG. 17 depicts a schematic of process steps a-u for fabrication of a capacitive pressure sensor on silicon substrate in accordance with one or more aspects of the present invention;

FIGS. 18A-18D depict a schematic of process steps in connection with fabrication of a dual layer differential flow sensor employing Al2O3 as an oxide etch barrier layer in accordance with one or more aspects of the present invention;

FIG. 20a depicts photograph views of test sensors with a single capacitor (top) and a dual-capacitor sensor (bottom) in accordance with one or more aspects of the present invention;

FIG. 20b depicts a photographic view of a flow control unit (syringe pump) and spectrometer (resonance frequency reader) with a test sensor on a chip carrier in accordance with one or more aspects of the present invention.

FIG. 20c depicts a schematic, cross-sectional view of an experimental set-up for testing a sensor in accordance with one or more aspects of the present invention;

DETAILED DESCRIPTION OF THE INVENTION

The following is a detailed description of the invention provided to aid those skilled in the art in practicing the present invention. Those of ordinary skill in the art may make modifications and variations in the embodiments described herein without departing from the spirit or scope of the present invention. Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, figures and other references mentioned herein are expressly incorporated by reference in their entirety.

As will be apparent to those skilled in the art, the terms "sensor" and "capacitor" may be used interchangeably when a capacitor is used as a sensor or vice-versa.

Uni-Capacitor Sensors

In accordance with one embodiment, a wireless uni-capacitor flow sensor with dynamic pressure and temperature equalization is disclosed. The wireless flow sensor is useful for both liquids and gases. Disclosed devices are intended to measure slow flow rates, such as occur in a shunt in a human eye or brain, but are capable of measuring a wide range of flow rates in biological, military and industrial applications. The devices use the deformation of a flexible capacitor plate due to the dynamic pressure of a flowing fluid as a means of converting the flow rate into a change in capacitance. The sensitivity of the flow sensor is improved by equalizing the static pressure of the fluid across the flexible capacitor plate. The devices are also insensitive to temperature variations. The flexible capacitor is connected with an inductor in a resonant circuit. Changes in the circuit resonance are calibrated initially with known flow rates. In operation, changes in the flow are determined from the circuit resonance using wireless electronics.

The devices can detect the flow rate after the shunt and indicate that the shunt is clogged or is failing. The uni-capacitor system disclosed herein overcomes the problem of background pressure variations which can produce signals in a bi-capacitor system that are 1000 times larger than the signal due to flow. These background variations need to be controlled to an extent that is impractical in a living patient.

With reference to the drawings, wherein like numerals indicate like elements, the following are exemplary of types of components that may be included in a smart shunt.

Figure 1:
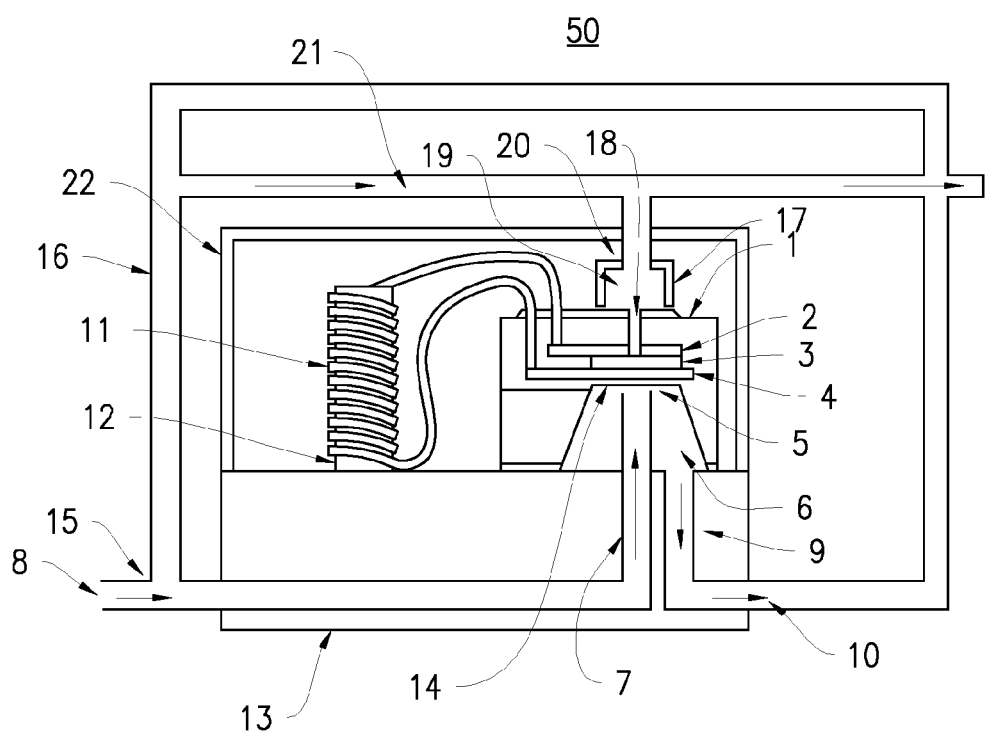
FIG. 1 is a schematic diagram of a flow sensor device in accordance with one or more embodiments of the present invention.

Referring to FIG. 1, an embodiment of a flow sensor device 50 may include a micro-electromechanical system (MEMS) sensor 1, which is a differential-pressure capacitor. The plates of the capacitor include the top metal plate 2 and bottom metal plate 4 that are separated by a distance 3, which is an air gap. The bottom capacitor plate 4 is operable to contact a flowing liquid through the tube 7 or with a controlled air pocket 7. Bottom capacitor plate 4 may contact a flowing liquid directly or through other layers formed on or adjacent capacitor plate 4, such that capacitor plate 4 may itself be a membrane or be a part of a membrane structure 14. The fluid enters the device at the inlet 8, flows out of the tube 7, through a gap 5 (which may be proportionally larger than that shown in FIG. 1), into the surrounding chamber 6 and exits the chamber 6 through the tube 9 out of the outlet 10. The pressure of the fluid in the chamber 6 causes the membrane 14 (and hence the capacitor plate 4, which in some embodiments may be the membrane) to deflect (deform) towards the top plate 2 and thereby reduce the separation between the two capacitor plates 2 and 4 and reduce the capacitance relative to that when no flowing fluid is present.

The fluid then goes through a tube with a calibrated flow resistance, R, to the back side of the same membrane. The device measures the pressure difference P1-P2 across the single membrane, where the flow rate, Vf, is given by $$Vf=(P1-P2)/R \qquad (1).$$

There are some applications for the flow sensor where the background, static pressure is not constant and has a range of variation that is orders of magnitude larger than the range of the pressure difference across the membrane. This would make it very difficult to separate the flow from the background. To alleviate this problem in accordance with one embodiment an apparatus is disclosed which may nullify the effect of static pressure on membrane deflection. A MEMS capacitor is constructed such that the gap 3 between the plates 2 and 4 has a vent 18 that allows the background pressure at the capacitor to be cancelled by the differential measurement. A second tube 16 is connected to the tube that carries the flowing liquid at a point 15, which is before the flowing fluid impinges onto the capacitor membrane 14. This second tube 16 allows part of the fluid to flow into the closed volume that includes the tube 16, the volume above the capacitor 19, and the gap between the plates 2. Before the liquid enters the device (initial condition) this closed volume is filled with air or some other gas. As the fluid starts to flow through the device, the fluid that flows into tube 16 pushes against the pressure of the air in the tube and will fill a volume up to a point 21. After the system equilibrates, there will be no flow in the tube 16 and the pressure in the tube will be just the static pressure of the fluid. Since the pressure in the tube must be the same in all places in the closed volume that includes the tube, the pressure at the top of the capacitor membrane 14 is the static pressure of the fluid. Since the pressure on the bottom side of the membrane also contains a component due to the static pressure of the fluid, the deflection of the membrane due to static pressure from the flowing fluid (bottom) is offset exactly (canceled) by the static pressure above the membrane. Therefore the net deflection of the membrane will only result from the pressure difference of the flowing fluid.

In most cases, for in vivo use of the device, the fluids that flow through the device are electrically conducting such as saline. It is important to keep the conductive surfaces of the capacitor plates insulated from the fluid since this would short the capacitor. One way to accomplish this is to deposit an insulating material on one of the two plates 2, 4 during the fabrication. A thin insulating layer on either plate would be possible, but applying the layer to the top capacitor plate 2 would provide the least complication to the design since it would not affect the mechanical properties of the thin membrane. Another consideration is that a liquid between the plates 2, 4 would change the dielectric properties of the gap 3 between the capacitor plates 2, 4. The dielectric property of the gap 3 affects the capacitance and the performance of the circuit that is used to sense the membrane deflection. It is important that, if it is possible to have a liquid between the capacitor plates, that this liquid be present at all times between the plates so that the device calibration will not change during normal operation. In one embodiment, to assure that liquid is between the plates 2, 4, the device is constructed such that the desired fluid can be flushed through the plates before the device is calibrated and used. This fluid should have the same dielectric properties of the fluid that will be used during operation of the device since, during the operation of the flow meter, the liquid between the plates will mix with the fluid that is being measured. Otherwise the fluid that it used to flush the plates will need to be immiscible with the fluid that is used in normal operation. Such a flow meter with fluid between the capacitor plates is a straightforward alternate embodiment of the devices detailed herein.

The capacitor plates may be coated with an insulating, inert fluid, such as an oil. To avoid the need for having fluid between the capacitor plates, in one embodiment the geometry of the closed volume (that comprises essentially the tube 16, the volume above the capacitor 19, and the gap 3 between the plates 2, 4) is designed such that liquid will not flow beyond the end of the tube 20. Initially there is no liquid in the tube and the pressure in the closed volume is $P_0$. The volume of air initially is $V_0+V_C$, where $V_0$ is the volume in the entire length, $L_0$, of the tube from point 15 to 20. $V_C$ is the remaining volume of air including the air above the capacitor and in the gap between the capacitor plates. When fluid is flowing through the flow meter the total volume of air in the closed volume, V, at equilibrium is $V_T+V_C$, where $V_T$ is the volume of air in the length, $L_F$, in the tube from the point 21 to 20, which is the end of the tube. When liquid is flowing through the device the pressure in the closed volume is $P_S$. One of the well-known laws of thermodynamics is that, for a gas, the product of the pressure times the volume is constant for a closed volume. That is, for the flow meter described here, $$P_0(V_0+V_C)=P_S(V_T+V_C) \quad (2)$$

and $$P_0(L_0A_T+V_C)=P_S(L_FA_T+V_C) \quad (3)$$

where $A_T$, is the cross-sectional area inside the tube. If the maximum allowable pressure, $P_{MAX}$, is defined as the pressure that compresses the liquid to the end of the tube (20), then with $L_F=0$, $$P_0(L_0A_T+V_C)=P_{MAX}V_C \quad (4)$$

$$L_0 = \frac{V_C}{A_T}\left(\frac{P_{MAX}}{P_0} - 1\right)$$

From Eq. 4 it can be further derived that a sufficient condition for the fluid to not reach the volume above the capacitor at the maximum designed static pressure, $P_{MAX}$, is that the total length of the tube, $L_0$, is long enough to assure that $$L_0 > \frac{V_C}{A_T}\left(\frac{P_{MAX}}{P_0} - 1\right) \quad (5)$$

Eq. 5 specifies the required relationship between the geometrical parameters $L_0$, $V_C$, and $A_T$ as a function of the pressures $P_0$ and $P_{MAX}$. In practice there may be other factors that constrain $L_0$, $V_C$, and $A_T$ including limitations of space. In particular, if the tube diameter $A_T$ is small to accommodate an interface to a shunt device for regulating intracranial fluid flow, then the volume $V_C$ will need to be small enough to keep $L_0$ from being unacceptably long. Since the device will be used in vivo, the flow meter will contain a cap 22 that hermetically seals it from the surroundings. In some embodiments the closed volume above the capacitor 19 may be smaller than the space within the cap 22 to limit $V_C$. Therefore, a cap 17 that is smaller than the cap 22 may be used to define the volume 19. The cap 17 may be hermetically sealed directly to the MEMS capacitor.

With the contribution from the static fluid pressure on the membrane deflection eliminated by the current invention, the capacitance, C, of the MEMS device is then a function of the pressure difference generated by the fluid flow rate and C is approximately given by the equation:

$$C = \frac{\varepsilon_0 A}{d}\left[1 + \frac{w}{2d}\right] \quad (6)$$

where $\varepsilon_0$ is the permittivity of free space, A is area of the capacitor plates, d is the initial separation or the capacitor plates, w is the deflection induced at the center of the membrane by the pressure, P, of the flowing fluid. w is given approximately by:

$$w = \frac{PA}{c_1 t\sigma} = \frac{\rho V_f^2 A}{2c_1 t\sigma A_T^2} \quad (7)$$

where $c_1$ is a dimensionless parameter, t is the thickness of the capacitor membrane, and $\sigma$ is the residual stress of the capacitor membrane. The MEMS capacitor is connected in series with an inductor 11 that includes wire wound around a suitable core material 12. The capacitor and inductor are mounted on a substrate 13. Alternate embodiments of this scheme include mounting the inductor directly on the MEMS device or fabricating the inductor on the MEMS device including using either of the metal levels that are used for the capacitor plates (2 or 4 in FIG. 1). An inductor fabricated into one of the metal levels of the MEMS structure may limit the inductance to much smaller values. The inductance is an important consideration for resonant frequency detection of the capacitance of the MEMS device.

Figure 1A:
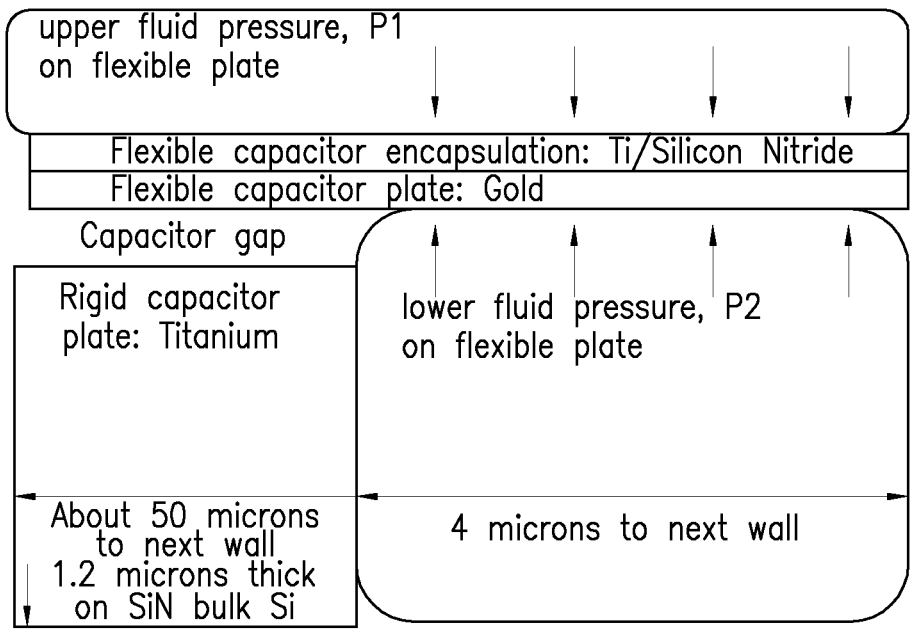
FIG. 1A is a schematic diagram of a flow meter using a differential capacitor plate in accordance with one or more embodiments of the present invention.

Now referring to FIG. 1A, another embodiment of a flow meter using a differential capacitor plate is shown.

Figure 2:
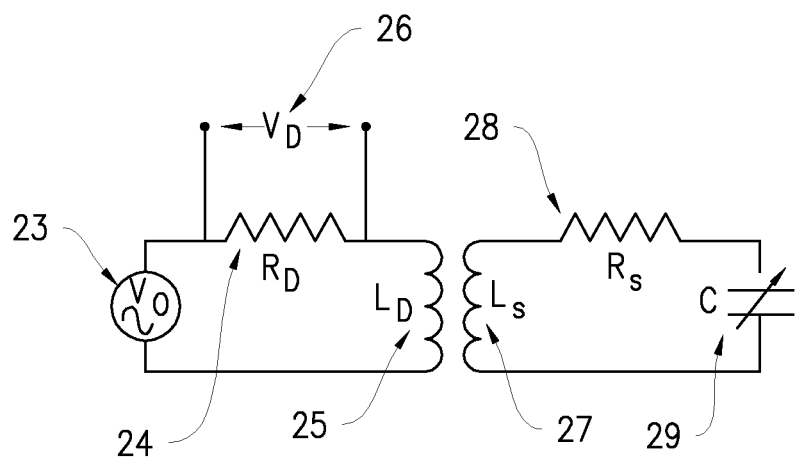
FIG. 2 is a schematic diagram of a device in accordance with one or more embodiments of the present invention.

Detection of the MEMS capacitance can be done using mutual induction, which is a technique that is well known to those who are knowledgeable in the art of wireless transmission technology. One embodiment is shown in FIG. 2. A flow sensor is represented by the variable capacitor 29 and is connected in a closed loop (sensor loop) circuit with an inductor 27. The resistor 28 in the sensor loop may only be the residual resistance of the interconnects and is important for calculating the quality factor, $Q_S$, of the sensor loop. The detection circuit includes an inductor 25 that is in close proximity to the inductor 27 in the sensor loop. The inductor 25 is driven with a sinusoidal voltage from 23 through a resistor 24 at a frequency, f. The varying electromagnetic field from inductor 25 induces a current to flow in the inductor 27. When the frequency f is such that the induced frequency in the sensor loop is at the resonant frequency $f_S$, which is $1/2\pi\sqrt{L_S C}$, a reverse current is induced in the inductor 25, which will cause a voltage drop across the resistor 24. By measuring the amplitude of the voltage 26 as a function frequency, f, the resonant frequency, $f_S$, can be detected as the frequency where the amplitude is at a minimum. The capacitance, C, of the MEMS capacitor is $1/L_S(2\pi f_S)^2$. Then equations (6) and (7) can be used to calculate the flow rate, $V_f$.

An important consideration for the flow sensor is the sensitivity, which is the ability to measure flow rates that are in the range of the flow rates for intracranial fluids. The intracranial flow rate may be as small as 20 milliliters per hour. There are two interrelated parts of the flow rate sensitivity that are important. The first is the mechanical sensitivity of the MEMS capacitor. The second is the relative error of the resonant frequency measurement, which relates to the quality factor, Q, of the measurement circuit. The first consideration concerns the deflection, w, of the membrane in response to the pressure of the flowing fluid and the corresponding change in capacitance that is induced. In equation 7 the thickness, t, of the membrane has to be large enough to be reliable under normal operating conditions. That is, the fracture strength of the membrane needs to be large enough to limit failure of the membrane within some specified range of pressure. The residual stress, $\sigma$, in the membrane is a key parameter since for many materials it can vary over several orders of magnitude depending on membrane growth method and processing conditions. Ideally the residual stress, $\sigma$, should be at a minimum and tensile to give the maximum pressure induced deflection of the membrane.

The following example parameters are used to estimate the sensitivity of the flow sensor:

TABLE 1

| Parameter | Description | Value | Unit |
| --- | --- | --- | --- |
| A | Area of capacitor plates | 4 | mm² |
| t | Membrane Thickness | 0.5 | micrometers |
| d | Initial spacing between capacitor plates | 4 | micrometers |
| $\sigma$ | Intial membrane stress | 1 × 10⁶ | Pascal |
| $\rho$ | Density of liquid (water) | 1 × 10³ | kg/mm³ |
| $\epsilon_0$ | Permittivity of free space | 8.85 × 10⁻¹² | MKS |
| c1 | Dimensionless parameter | 3.393 | |
| $L_S$ | Inductance of sensor coil | 0.01 | henry |
| $R_S$ | Resistance of sensor loop | 0.21 | ohm |
| $L_D$ | Inductance of detector coil | 0.001 | henry |
| $R_D$ | Resistance of detector resistor | 1 × 10⁶ | ohm |
| M | Mutual induction between $L_S$ and $L_D$ | 0.0001 | henry |
| $V_D$ | Amplitude of detector drive voltage | 5 | Volts |

Figure 3:
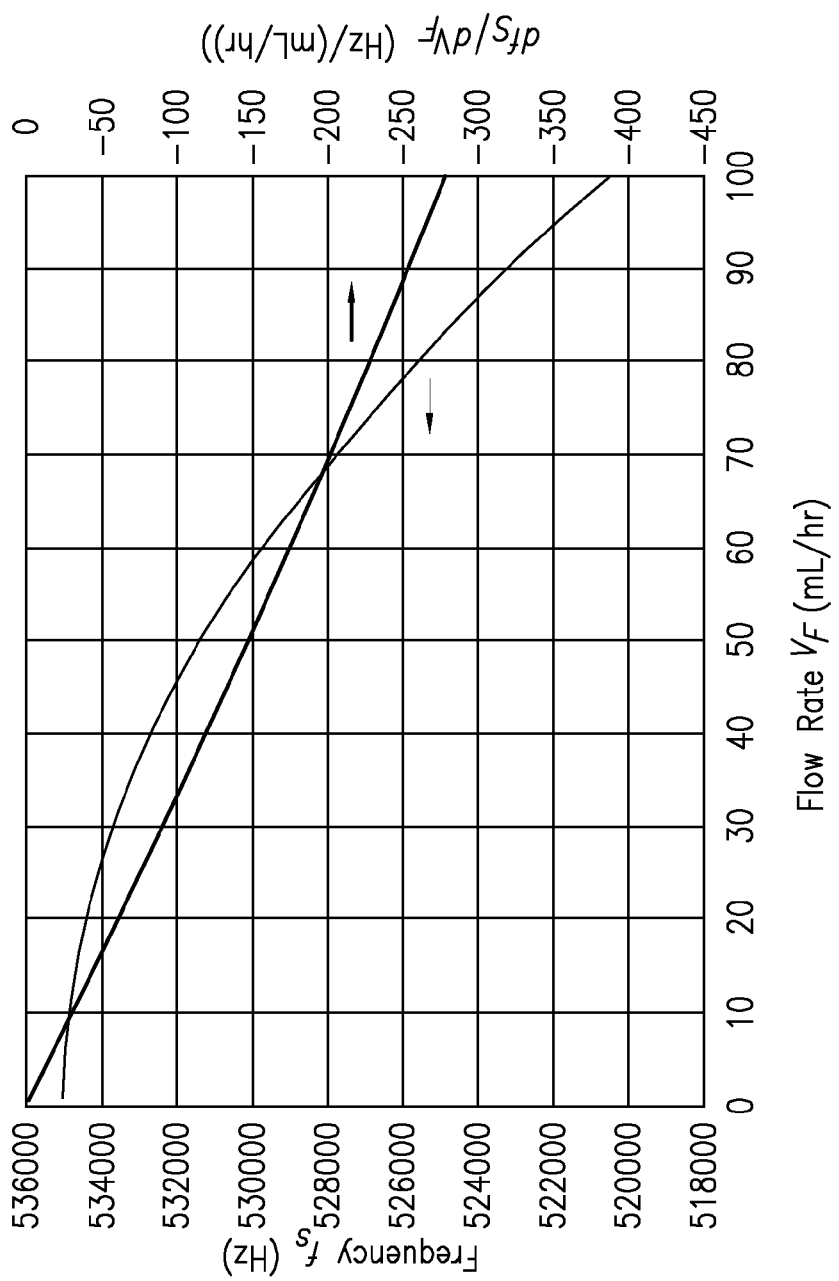
FIG. 3 is a graphical representation of the resonant frequency, $f_S$, of the sensor loop plotted as a function of the flow rate, $V_F$, along with the derivative of $f_S$ with respect to $V_F$ according to one or more further aspects of the present invention.

Now referring to FIG. 3, using equations 6 and 7 with $f_S=1/2\sqrt{L_S C}$, the resonant frequency, $f_S$, of the sensor loop is plotted as a function of the flow rate, $V_F$, along with the derivative of $f_S$ with respect to $V_F$. From FIG. 3 it can be seen that at $V_F$=20 milliliter/hour $df_S/dV_F \cong -60$ Hz per milliliter/hour. That is, at $V_F$=20 milliliter/hour, if the flow rate increases by 1 milliliter/hour, the resonant frequency will be shift downward approximately 60 Hz. The half-width-half-maximum (HWHM) of the frequency $f_S$ can be used as an estimate of the intrinsic error, $\Delta f_S$, of the measurement of $f_S$ and can be estimated from quality factor, $Q_S$, of the sensor. $\Delta f_S$ is then given by $$Q_S = 2\pi f_S \frac{L_S}{R_S} \quad (8)$$

$$\Delta f_S = \frac{f_S}{Q_S} = \frac{R_S}{2\pi L_S}$$

Using the values in Table 1, $\Delta f_S$ is approximately 3.3 Hz which is much smaller than $df_S/dV_F$ (60 Hz) at $V_F$=20 milliliter/hour.

Figure 4:
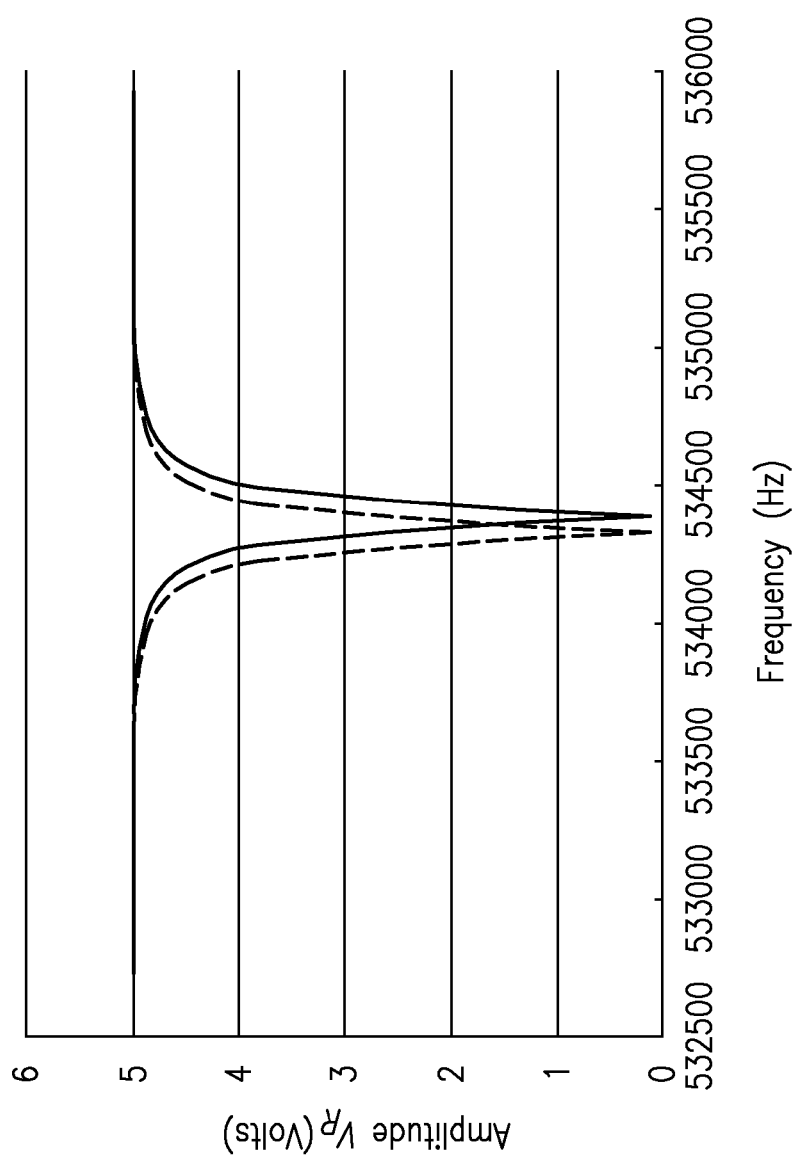
FIG. 4 is a graphical representation of the amplitude of the voltage across the resistor $R_D$ calculated as a function of frequency according to one or more further aspects of the present invention.
Figure 5A:
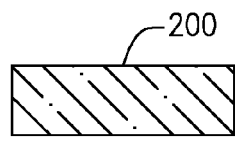
FIG. 5 is a series of drawings depicting process steps a-x for fabricating a flow sensor in accordance with one or more aspects of the present invention.
Figure 5B:
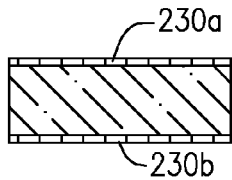
Figure 5C:
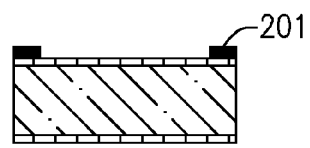
Figure 5D:
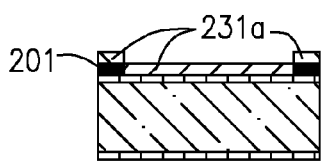
Figure 5E:
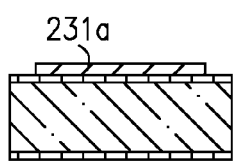
Figure 5F:
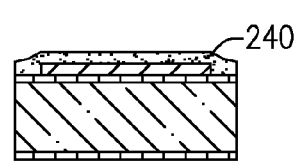
Figure 5G:
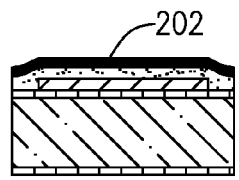
Figure 5H:
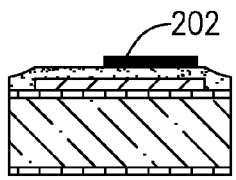
Figure 5I:
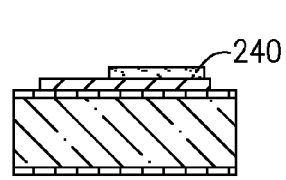
Figure 5J:
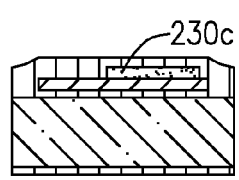
Figure 5K:
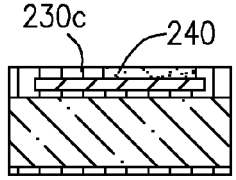
Figure 5L:
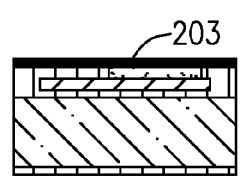
Figure 5M:
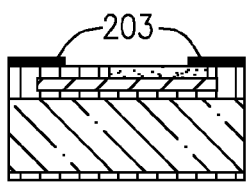
Figure 5N:
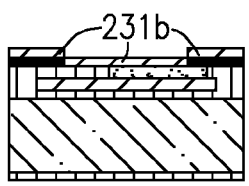
Figure 5O:
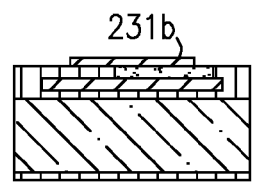
Figure 5P:
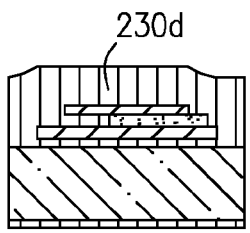
Figure 5Q:
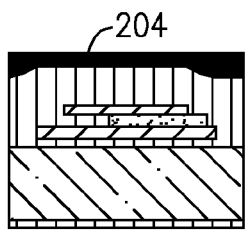
Figure 5R:
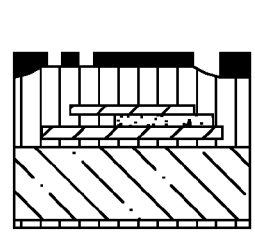
Figure 5S:
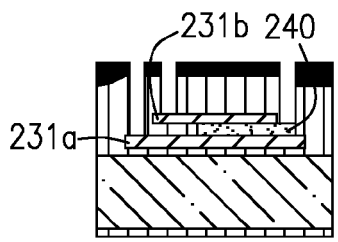
Figure 5T:
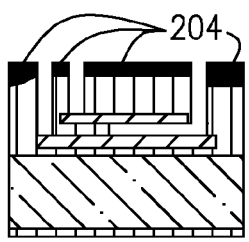
Figure 5U:
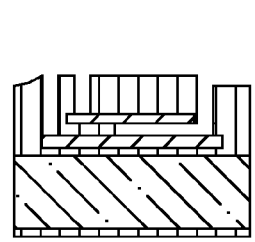
Figure 5V:
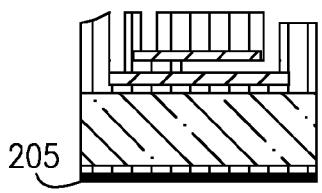
Figure 5W:
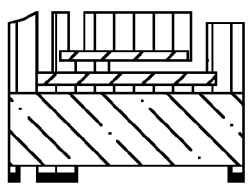
Figure 5X:
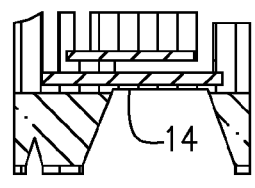

The mutual induction, M, between the detection and sensor coils shown in FIG. 2 is important for obtaining a large enough voltage drop at the resonant frequency for maintaining the sensitivity to flow rate. Using advanced materials such as Super Permalloy, high inductances can be achieved in a small space to make both the sensor and detector circuits practical. Now referring to FIG. 4, using the values in Table 1 the amplitude of the voltage across the resistor $R_D$ can be calculated as a function of frequency for $V_F$=20 and 21 milliliter/hour. These examples are shown to indicate that there is a set of material parameters that are achievable using available components and fabrication techniques to give an acceptable level of sensitivity for detecting flow rates in the 10 to 100 milliliter/hour range. Further optimizations of these parameters may improve the sensitivity or make the device practical for other ranges of flow rates.

Now referring to FIG. 5, one embodiment of a process is described for fabricating a MEMS capacitor, an important component of the flow sensor. The sensor can be constructed from materials that are in common use in MEMS and other semiconductor devices. One skilled in the art will recognize there may be other materials that will achieve the needed device performance.

In accordance with one embodiment, in FIG. 5 (step a), a silicon wafer 200 is provided oriented in the [001] direction to facilitate anisotropic etch steps. Silicon nitride layers 230a, 230b ($SiN_x$) are deposited on both sides of the wafer (FIG. 5 step b). The topside layer 230a may be low-stress $SiN_x$ and be part of a membrane structure that will flex under the pressure of a flowing liquid. The thickness of the top layer 230a of $SiN_x$ (~0.5-1.0 micrometers) is small enough to give the required sensitivity for and thick enough to be robust with high fracture strength. The bottom side $SiN_x$ deposition layer 230b may be patterned later in the process to define the surface area of the membrane and to define the location of V-groove scribes on the wafer to facilitate separating individual devices after processing. Photolithography is employed to deposit resist and pattern for a first metal layer 231a deposition (FIG. 5 step c). The pattern will define the bottom capacitor plate, electrical interconnect between the bottom capacitor plate and a first contact pad ("contact pad 1"), and contact pad 1. Metal layer 231a is deposited over the developed resist pattern 201 (FIG. 5 step d). Metal layer 231a may be a bi-layer consisting of Cr (~5 nm) for adhesion and W or TiW (~10 nm). The stress of this film should be minimized to keep the flexible membrane stress tensile but at a minimum. Balancing the compressive and tensile stresses of the metal components minimizes the bi-layer stress. The resist 201 and metal 231 that covered the resist are removed leaving desired metal 231a pattern (FIG. 5 step e). Referring to FIG. 5 step f, silicon oxide layer 240 ($SiO_2$) is deposited as a sacrificial layer. The $SiO_2$ thickness (~2-10 micrometers) will set the separation between the two plates of the capacitor. Referring to FIG. 5 step g, photoresist 202 is deposited. The photoresist 202 is patterned, leaving resist to define the area of the capacitor (FIG. 5 step h). $SiO_2$ 240 is removed from unpatterned areas and remaining resist 202 is removed using reactive ion etch (RIE) (FIG. 5 step i). $SiN_x$ support layer 230c is deposited (FIG. 5 step j). The $SiN_x$ support layer 230c is deposited with a thickness larger than the capacitor plate separation, since the final thickness will be set by the next step in the process. Referring to FIG. 5 step k the SiNx support layer 230c is chemical-mechanical-polished (CMP) to the thickness of the $SiO_2$ sacrificial layer 240. The CMP removes the topography and leaves a flat surface for the second metal layer 231b deposition. Referring to FIG. 5 step 1, photoresist 203 is deposited. Photoresist 203 is patterned to define the top capacitor plate, electrical interconnect between the top capacitor plate and a second contact pad ("contact pad 2"), and contact pad 2 (FIG. 5 step m). Second metal layer 231b is deposited (FIG. 5 step n). Metal of layer 231b is preferably a bi-layer which may include Cr (~5 nm) for adhesion and W or TiW (~10 nm). The stress of this film should be minimized to keep the fixed membrane stress at a minimum. Balancing the compressive and tensile stresses of the metal components minimizes the bi-layer stress. Referring to FIG. 5 step o, resist 203 and metal of layer 231b that covered the resist are removed leaving a desired metal 231b pattern. With reference to FIG. 5 step p, a $SiN_x$ top structural layer 230d is deposited. The $SiN_x$ top structural layer 230d should be thick enough (~10 micrometers) to be relatively rigid to small vibrations that could introduce noise to the capacitance. Photoresist 204 is deposited (FIG. 5 step q). Photoresist 204 is patterned to uncover the two contact pads and windows to the sacrificial SiO2 layer (FIG. 5 step r). $SiN_x$ 230d is etched (RIE) down to contact pads (layers 231a, 231b) and the SiO2 layer 240 (FIG. 5 step s). The sacrificial $SiO_2$ layer 240 is etched using hydrofluoric acid solution (FIG. 5 step t). Photoresist 204 is removed (FIG. 5 step u). Photoresist 205 is deposited on a backside of the wafer (FIG. 5 step v). Photoresist 205 and RIE $SiN_x$ layer 230b are patterned to define a bottom membrane area and V-grooves (FIG. 5 step w). Since an anisotropic Si etch (KOH) is used, the pattern area will be larger than the final area. The pattern is oriented to etch the 111 planes in the silicon 200, which are at a 54.7 degree angle to the surface normal. Referring to FIG. 5 step x, silicon 200 is etched anisotropically in KOH solution to release the membrane. If metal 231a or 231b etches in KOH, the top surface should to be protected. Placing the wafer in a holder that seals the front side from the KOH can protect the front surface.

In another embodiment, a MEMS capacitor may be formed by two rigid chip structures bonded together, each of the chips including a flexible membrane. Such a capacitor may employed to form a sensor including two flexible capacitor plates separated by a distance forming a gap, wherein the flexible capacitor plates include membrane structures operable to contact a fluid and deform in response to pressure exerted by the fluid, wherein the device is operable to convert deformation of the membranes into a change in the resonant absorption of a capacitor-inductor loop.

Pressure Sensor

Figure 6:
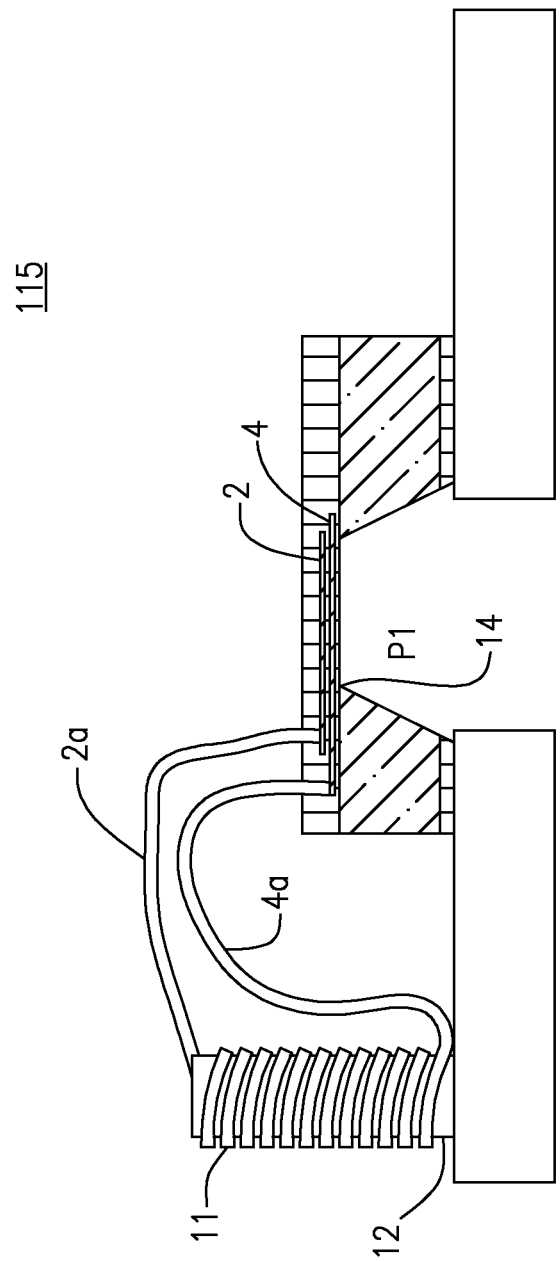
FIG. 6 is a schematic depiction of a pressure sensor in accordance with one or more aspects of the present invention.

Now referring to FIG. 6, a pressure sensor 115 may be placed on the end of a shunt tube (in the ventricle of the brain, for example) where the pressure will be undisturbed by the shunt. Wires may be disposed to extend to near the surface of the body where a coil may be positioned for coupling to the external wireless measuring system. The pressure sensor 115 may be the same as the basic MEMS component of the flow sensor, but without pressure balancing and without the force of the flowing fluid on the flexible capacitor.

In the pressure sensor 115, no flow is required and only the pressure is transmitted through the fluid to the region P1 below the bottom capacitor plate 4. The gap between the capacitor plates 2, 4 may be, and is preferably, at a fixed pressure which would be sealed in by the layer containing the top, fixed capacitor 2 plate during fabrication. Each of the capacitor plates 2, 4 are attached to a wire 2a, 4a, respectively, which connects to an inductor 11 in the form of a coil. This coil may be remote from the capacitor and part of the coil may serve as an antenna for probing the resonant properties of the circuit. As in the case of the flow sensor, changing pressure near the capacitor moves the free membrane 14 and changes the capacitance. The changing capacitance in turn changes the resonant property of the circuit, which may be measured wirelessly. The sensor 115 may be calibrated after fabrication by measuring it in a fluid of known pressure. The calibration may also include a measurement of the effect of temperature (since increased temperature would expand the fluid between the capacitor plates 2, 4 and mimic a pressure reduction). A temperature correction may be included in the measurement electronics. Using MEMS type technology, this device may be made small enough to incorporate in a shunt for the treatment of glaucoma and the associated monitoring of the intraocular pressure.

Fluid Composition Sensor

Figure 7B:
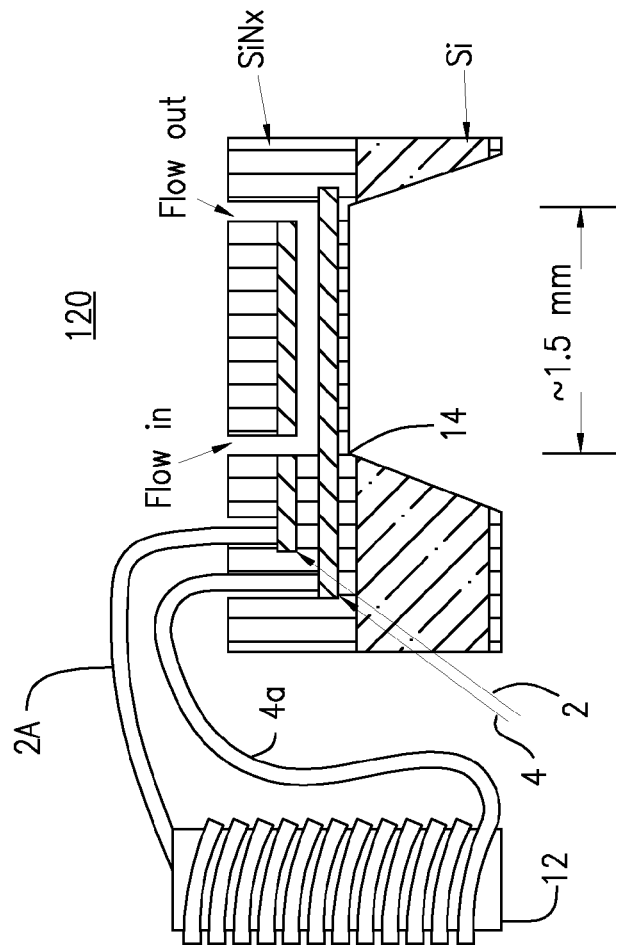
FIG. 7B is a schematic, side cross-sectional view of a fluid composition sensor in accordance with one or more aspects of the present invention.
Figure 7A:
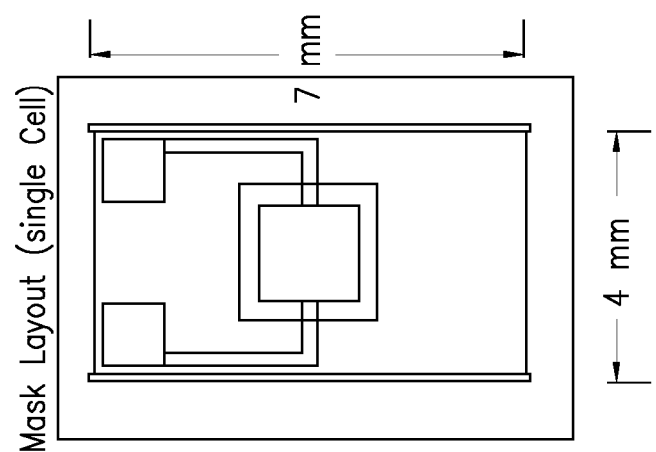
FIG. 7A is a top plan view of a mask layout for a fluid composition sensor in accordance with one or more aspects of the present invention.

With reference to FIG. 7A, an exemplary mask layout for a fluid composition sensor is shown. With reference to FIG. 7B, fluid flows into the sensor 120 as shown. This flow proceeds through the device 120 between the capacitor plates 2, 4 and out the other side. In this embodiment, the same fluid pressure may be present on both sides of the capacitor plates 2, 4, so that it would be insensitive to both temperature and pressure. In a preferred embodiment, the composition sensor 120 may be run in parallel to the main channel of the shunt, so as to avoid impeding the main flow given that the spacing between the capacitor plates 2, 4 would be smaller than the main channel to enhance the sensitivity of the device.

The device 120 functions under the assumption that the fluid contains solutes of some kind, such as salt in the cerebro-spinal fluid. As the concentration of the solvent varies, both real and imaginary part of the dielectric constant in the capacitor varies. This variation is measured by the resonance of the circuit including the capacitor and inductor 11, providing an indication of the composition of the fluid. In the case of the salt in the cerebro-spinal fluid, the conductivity of the fluid would change substantially, the capacitor loss would respond and the width of the resonance would allow an indication of the fluid composition. The shape of the absorption resonance of the LC circuit may be modified by the dielectric constant of the constituents of the fluid and provide information about them. The device may be calibrated after fabrication by immersing it in appropriate fluid and recording the changes in resonance under controlled compositions.

The composition sensor 120 may be employed to measure the normally occurring variations so that the physician would have a better understanding of a particular patient. It also serves to monitor directly the effect of medication in the fluid.

Flow Restoration Component

Figure 8:
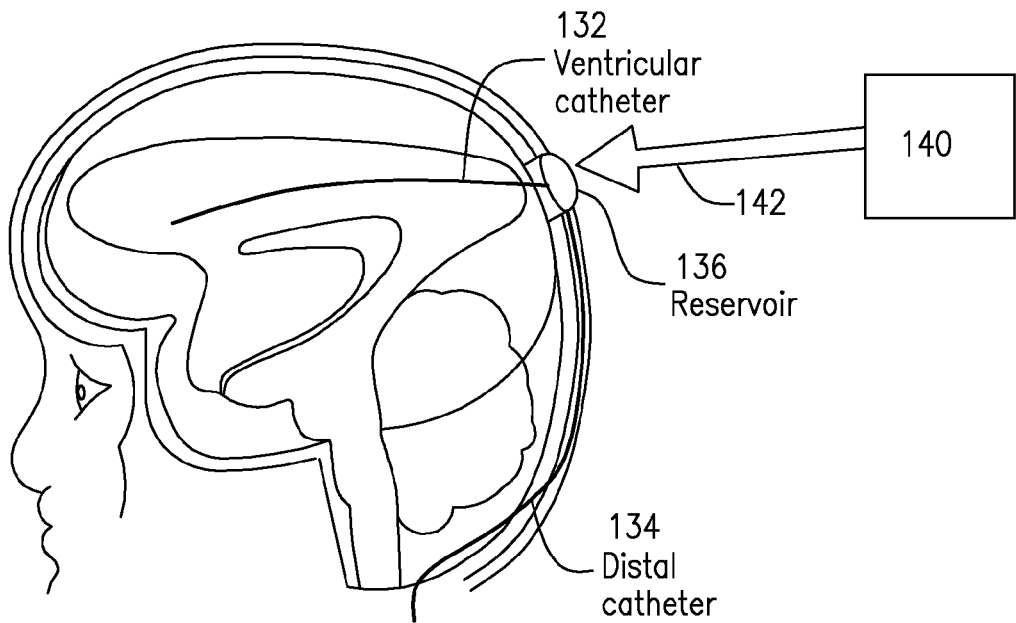
FIG. 8 is a schematic depiction of a flow restoration component in accordance with one or more aspects of the present invention.

With reference to FIG. 8, a device 130 is disclosed having a ventricular catheter 132, distal catheter 134 and reservoir which is operable to restore flow in the event of an occlusion. A strong pulse 142 of sonic power delivered from a external sonic generator 140 vibrates a flexible membrane under the skin at an angle of the ventricular catheter 132 under the skin and produces an ultrasonic pulse in the fluid. The external sonic generator 140 is placed just outside the ventricular catheter 132 at a position where the sonic pulse is coupled to the membrane in the shunt and aimed down the catheter in which it will be channeled to the distal end of the ventricular catheter 132 placed deep in the ventricle of the brain, where evidence indicates that most shunts are likely to clog.

The device 130 may be coupled to a capacitor which in turn is coupled to a wireless circuit that delivers power to the implanted part of the device 130. In this case, the moveable plate in the capacitor is comparable in size to the shunt and is strong enough to be driven electrically to produce a substantial pressure pulse. The pulse travels down the ventricular catheter and is absorbed in the region near the end of the catheter. In a preferred embodiment a train of pulses in the form of solutions may be used. Losses in the shunt tube are not problematic because the tube length is often short. The energy of the pulse is partly reflected from the shunt end, but mostly absorbed in damped vibrations. These vibrations tend to dislodge particulate matter from the openings near the shunt end, thus clearing the intake openings. When the openings are clear, the pressure waves tend to drive particles away from the openings, thus lengthening the time before the next clearing would be required.

A range of pulse sizes, widths and frequencies are available through the external electronics.

In various embodiments of this flow restoration device, it may be paired with designs of the fluid intake device to optimize the function of both. In one embodiment, the end of the ventricular catheter 132 may be covered with a meshwork which may be directly in the path of the pressure pulse propagation direction.

Flow Regulation Component

Figure 9:
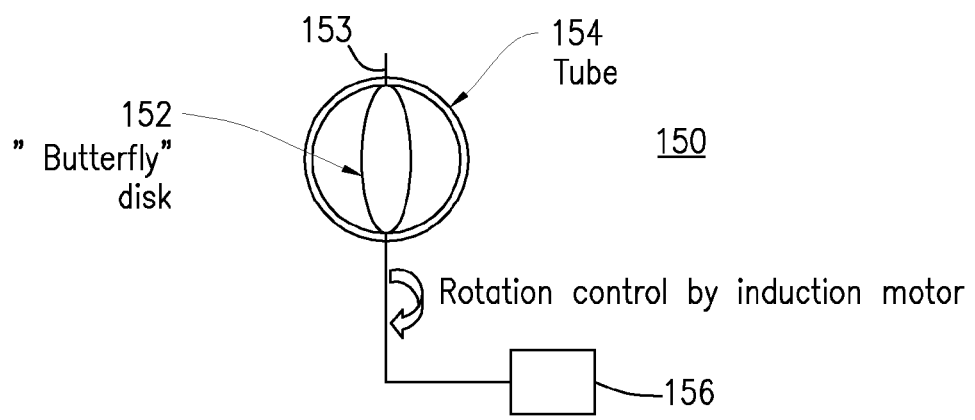
FIG. 9 is a schematic depiction of a flow regulation component in accordance with one or more aspects of the present invention.

With reference to FIG. 9, in accordance with an embodiment, a flow regulation component 150 may include essentially a flow regulation valve 152 placed directly in the shunt tube 154, at a point where it can be strongly coupled to the motor 156, which could be either external or implanted.

In one embodiment the valve is a butterfly valve 152 which is rotatable about a shaft 153 which provides friction so that under normal flow conditions the valve does not move. When the disk in the valve 152 is open it is in the plane of the flow and provides only negligible impedance to the flow. The disk can be continuously rotated and, when closed, would essentially stop the flow. The shaft 153 may have an end exterior of the shunt tube which may be connected to AC motor coils which allow a signal from a flow or pressure meter to change the position of the valve. Advantages of this embodiment include controllability of the valve and the ability of the valve to respond immediately to abnormalities in the fluid, and, if desired, correct for the pulsatile component of the pressure in fluids such as cranial fluids, ocular fluids and blood.

External Wireless Communication

When small coupling powers are required, the external communicator may be a combination of a microprocessor, a special antenna and a cell phone and could be easily portable. For more intense coupling power and more detailed processing links to external power and computing equipment may be desirable.

Figure 10:
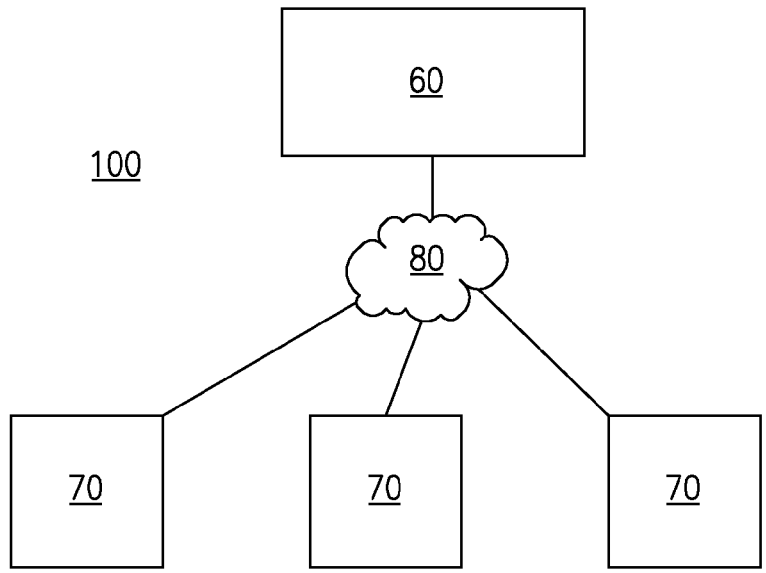
FIG. 10 is a block diagram of a network system suitable for carrying out methods in accordance with one or more embodiments of the present invention.

Referring now to FIG. 10 a block diagram illustrates an example of a system 100 for providing output from sensors to a communication system that is operable to provide information to a care provider located remotely.

The system 100 preferably includes at least one server 60 coupled to one or more user computers 70 over a network 80, such as the Internet. The server 60 and user computers are operable to carry out computing activity (e.g., the execution of suitable software code) in connection with implementing the functions and actions of the system 100 disclosed and described herein.

By way of example, the server 60 and/or the user computers 70 may be implemented using known hardware, firmware, and/or software, as well as specialized software for carrying out specific functions and actions desirable for implementing embodiments of the invention. For example, with reference to FIG. 11, the server 60 and/or the user computers 70 may include a computer 101, which includes a data processing unit (or processor) 102 and a memory 104 operatively coupled by way of a data and/or instruction bus 106. The processor 102 may be implemented utilizing any of the known hardware, such as a digital microprocessor, a computer (such as a portable, a stationary and/or a distributed computing system), or any of the other known and/or hereinafter developed data processing units. The memory 104 may be implemented by way of separate hardware or may be disposed within the data processing unit 102, and any of the known hardware and/or software for implementing the memory function may be employed.

Data are preferably input to, and output from, the data processing unit 102 by way of an input/output device (or I/O interface) 108. Operators of the system 100 may desire to input software programs and/or data into the computer 101 by way of an external memory 110 that is coupled to the I/O interface 108 by way of a suitable link (such as a cable, wireless link, etc.) The external memory 110 may be implemented via a flash-drive, disc, remotely located memory device, etc.

The server 60 and/or the user computers 70 may also include an interface device 111, which is operatively coupled to the I/O interface 108 of the computer 101 via a suitable link, such as a cable, wireless link, etc. The interface device 111 includes at least one display 112, as well as an input device 114, such as a keyboard, mouse, voice recognition system, etc. The operators of the system 100, such as an IT professional (on the server 60 end) or a researcher (on the user computer 20 end), preferably utilizes the interface device 111 to provide information to the computer 101 in connection with entering appropriate data and/or programs into the system 100.

The computer 101 manipulates data via suitable software code in accordance with various embodiments of the invention and may display results on the display 112 for consideration by the various operators (IT professionals, users, etc.). In accordance with well-known techniques, the results may also be stored within the memory 104 of the computer 101, output and saved on the external memory device 110, and/or provided in any of a number of other ways.

Figure 11:
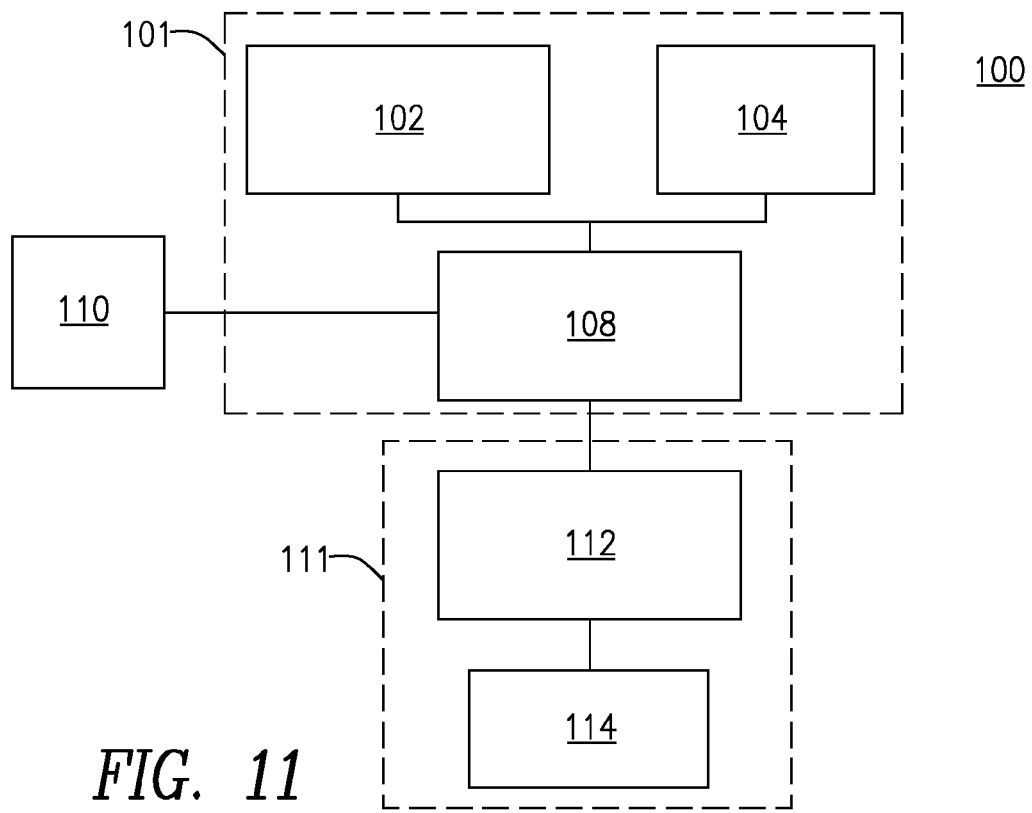
FIG. 11 is a block diagram of a computing system suitable for carrying out methods in accordance with one or more embodiments of the present invention.

It is noted that the functional blocks illustrated in FIGS. 10-11 may be partitioned as shown or may be partitioned in any other way, such as in an integral fashion. By way of example, the system 100 may be implemented utilizing a portable, stationary, or distributed computer operating under one or more suitable computer programs. Further, one or more of the functional blocks of the system 100 may be remotely located from the others, such as in a distributed (e.g., networked) system.

Irrespective of how the system 100 is implemented and/or partitioned, it preferably carries out one or more methods for providing output from one or more sensors associated with a smart shunt to a communication system that is operable to provide information to a care provider located remotely.

Figure 12:
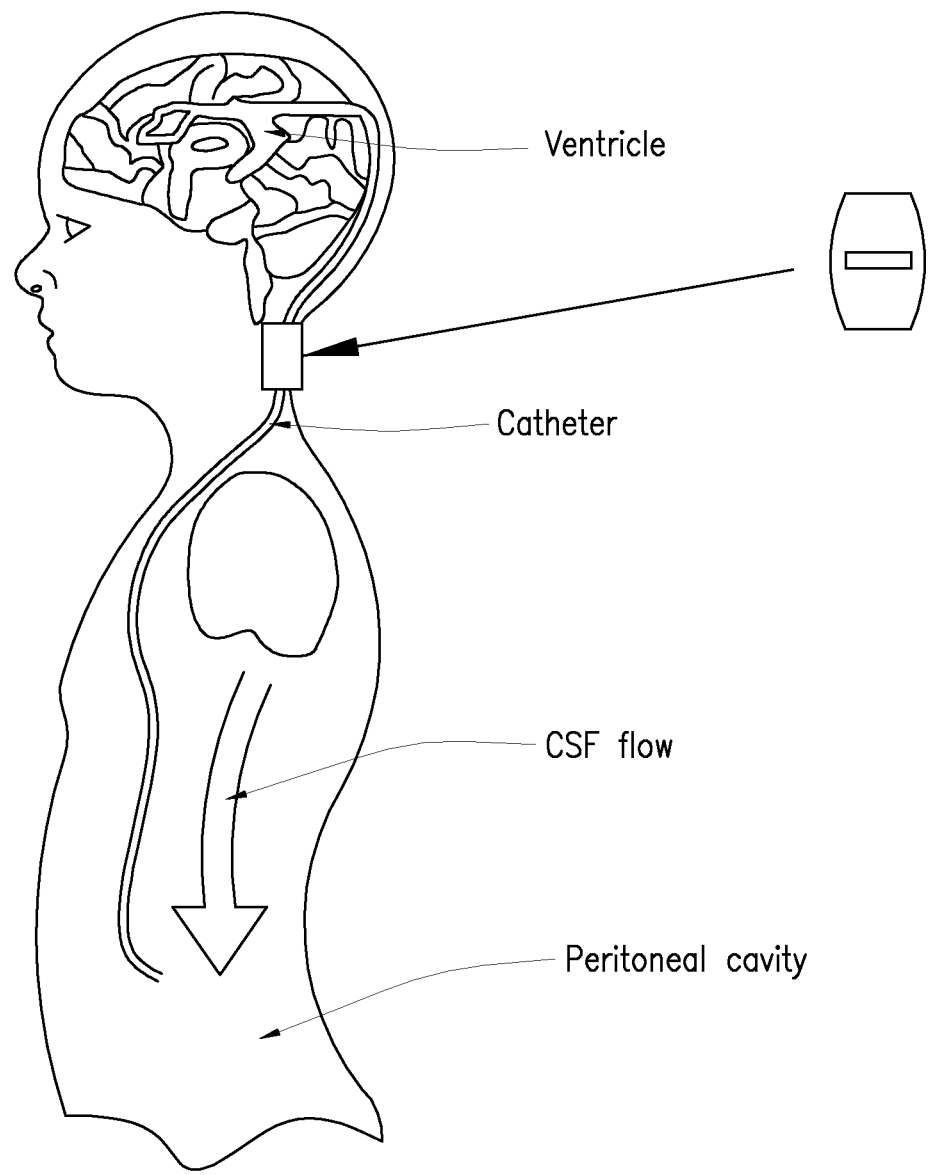
FIG. 12 depicts an embodiment of the invention implanted in a human in accordance with one or more embodiments of the present invention.
Figure 13:
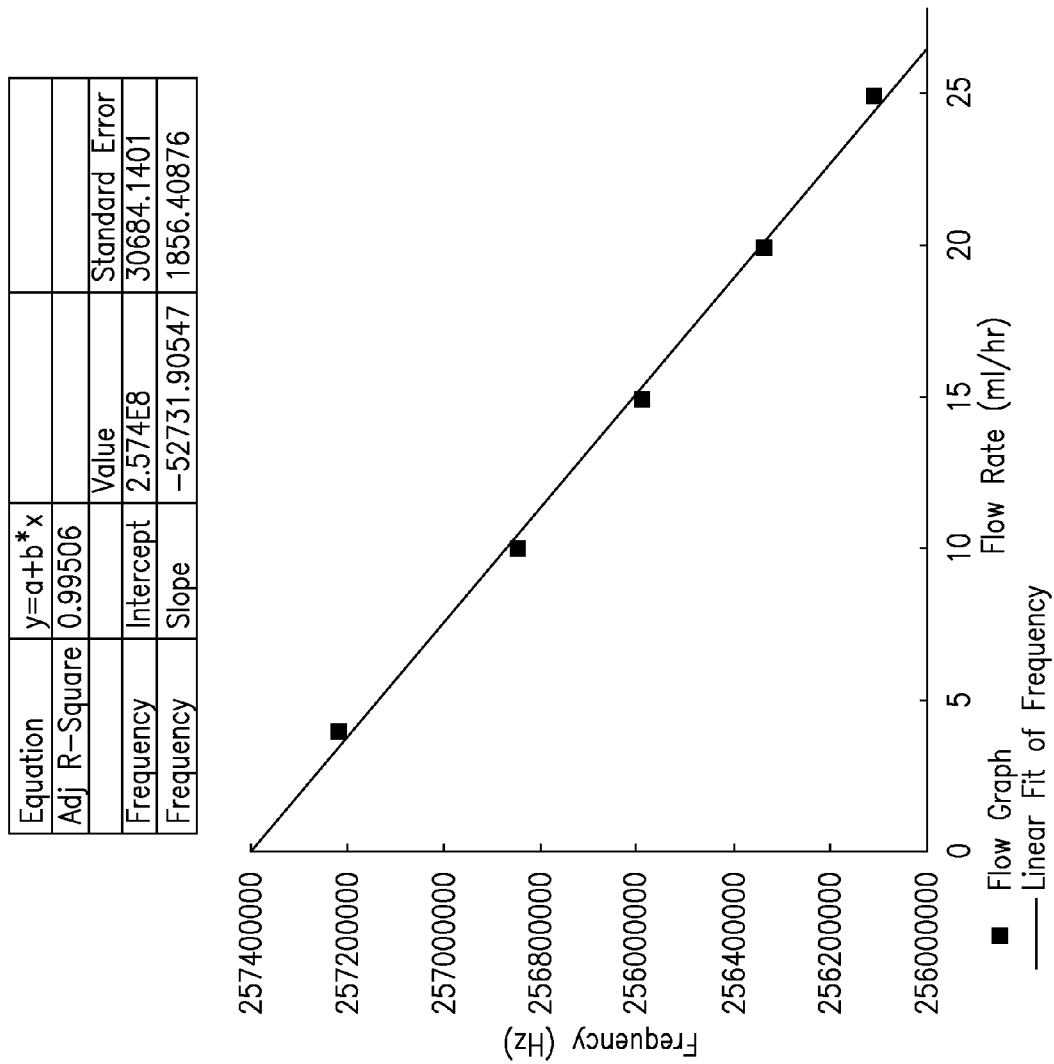
FIG. 13 is a graphical depiction of flow rate versus frequency in accordance with one or more embodiments of the present invention.
Figure 14:
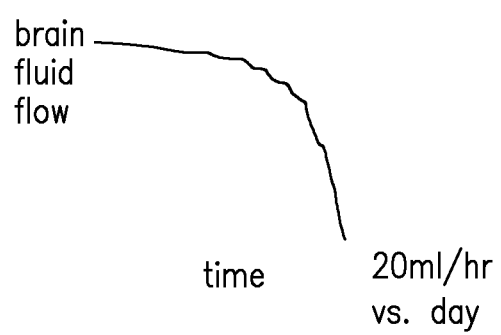
FIG. 14 is a graphical depiction of flow rate versus time in accordance with one or more embodiments of the present invention.

Now referring to FIGS. 12-14, in accordance with one embodiment a method is provided which includes implanting in a patient a smart shunt with the capability of measuring pressure and flow rate in the shunt as a function of time. The patient is typically one with hydrocephalus or other brain injury that leads to an unhealthy condition of fluid pressure and flow in the cerebrospinal fluid system. A study is made of the patient's cerebrospinal fluid flow, pressure or both as a function of time under controlled conditions to serve as a control. A treatment is administered to the patient. This treatment may consist of drugs, change in eating or drinking, change in activity or other factor that is believed to benefit the patient's condition. A study is made of the patient's cerebrospinal fluid flow, pressure or both as a function of time under the same controlled conditions as in the control measurement. The length of time is long enough to allow the treatment to take effect, which may be less than an hour for some ingested substances and may be longer than several months for changes in activity. The cerebrospinal fluid flow, pressure or both as a function of time is compared for the test and the control. The test is repeated to determine the reproducibility of the results. The results may be made available for utilization. The methods herein are intended to evaluate both beneficial and deleterious effects. Deleterious effects may include the treatments listed as examples above, but also include other uncontrolled (but potentially controllable) effects such as occlusion of the shunt, and controllable effects such as forces on the patient due to gravity and acceleration.

In one embodiment a method of testing a shunt itself is disclosed for evaluating the precursive behavior to occlusion of the shunt to improve decisions on shunt revision. See, Published U.S. Patent Application 2010/0228179 "No Clog Shunt Using a Compact Fluid Drag Path", the entirety of which is incorporated herein by reference. The method can be used in a brief examination of the shunt in the operating room after the ventricular end is inserted in the head. Occlusion can be detected very quickly by testing the flow of cerebrospinal fluid.

Dual Capacitor Sensors

In accordance with another embodiment, dual capacitor flow sensors are provided.

Dual capacitor sensors as disclosed herein are capable of measuring the slow flow characteristic of the cerebrospinal fluid in the range from less than 4 mL/hour to above 100 mL/hour. These sensors are suitable for long-term implantation at least in part because they use a wireless external spectrometer to measure passive subcutaneous components. The sensors are pressure-sensitive capacitors, in the range of 5 pF with an air gap at atmospheric pressure. Each capacitor is in series with an inductor to provide a resonant frequency that varies with flow rate. At constant flow, the system is steady with to <0.3 mL/hr over a month. At variable flow rate, $\dot{V}$, the resonant frequency, $f_0$, which is in the 200-400 MHz range, follows a second order polynomial with respect to $\dot{V}$. For this sensor system the uncertainty in measuring $f_0$ is 30 kHz which corresponds to a sensitivity in measuring flow of $\Delta\dot{V}$=0.6 mL/hr. Pressures up to 20 cm $H_2O$ relative to ambient pressure can also be measured. An implantable twin capacitor system is provided that can measure flow, which is fully compensated for all hydrostatic pressures.

The dual capacitor smart shunts disclosed herein employ an implanted pair of capacitive pressure sensors made using MEMS technology to monitor flow and provide early warning of a shunt failure. The devices are sensitive enough to allow the detection of the approach to shunt occlusion and to monitor the efficacy of treatments. Such devices may allow a physician to check for failure of CSF flow without surgery and make an informed and quick decision about further diagnosis and treatment.

For a fuller understanding of the embodiments herein it useful to discuss some of the underlying theory of sensor operation.

Theory of Sensor Operation

Pressure drop due to viscous drag along the walls of a tube when fluid flows through, is governed by Poiseuille's law. The flow rate of the fluid produces a dynamic contribution to the pressure drop. The difference in pressure, $\Delta P$, between two points in the flow is proportional to the volumetric flow rate, $\dot{V}$:

$$\Delta P = -R_{hyd}\dot{V}, \qquad (11)$$

where $R_{hyd}$ is the hydraulic flow resistance, which depends on the geometry of the channel between the two points where the pressure is measured and the viscosity, $\mu$, of the fluid. For a circular cross-section channel with diameter, D, and length, l, it is:

$$R_{hyd} = \frac{128}{\pi}\mu\frac{l}{D^4} \qquad (12)$$

The pressure sensor employed in one or more embodiments is a parallel plate capacitor with a fixed upper plate and a flexible lower plate designed to be in contact with the fluid. The pressure of the fluid pushes against the lower plate and the deflection produces a change in the distance between the capacitor plates, thus resulting in a change in capacitance. The capacitance change is directly proportional to the fluid pressure. The capacitor is connected to an inductor, which is inductively coupled to a spectrometer that allows for wireless detection of the flow or pressure.

For a square membrane with a half-width, a, the pressure changes the capacitor gap, w, at the center. The area is $a^2/4$, (a square supported on all sides). The pressure is given by $$P = \frac{c_1\sigma_0 tw}{a^2} + \frac{c_2 Etw^3}{a^4(1-v)}, \qquad (13)$$

where $c_1$=3.393, $c_2$=8/6(1+v), $\sigma_0$ is the initial stress of the membrane, t is the thickness of the membrane, E is the Young's modulus and v is Poisson's ratio. For the $SiN_x$ membrane that was fabricated for certain embodiments herein the Young's modulus E is 220 MPa, v is 0.28 and $\sigma_0$ is from 100 MPa to 400 MPa. For membrane stresses in $SiN_x$ that are in this range the first term on the right hand side of Equation 13 is much larger than the term proportional to $w^3$. That is, the center deflection is a linear function of the pressure. The sensor is more sensitive when the initial membrane stress is smaller, but should be optimized along with the area, membrane thickness, and capacitor plate spacing to minimize the chance that the plates touch at the maximum design pressure.

The capacitance is calculated by first modeling the shape of the membrane under pressure either by using an analytical formula or finite element analysis. For a square membrane w is replaced by w(x,y) with $-a \leq x \leq a$ and $-a \leq y \leq a$. An analytical model as follows was used in connection with the embodiments herein:

$$w(x, y) = w_0 \cos\left(\frac{\pi x}{2a}\right) \cos\left(\frac{\pi y}{2a}\right) \quad (14)$$

where $w_0 = w(0,0)$ is the deflection at the center of the membrane and includes contributions from the pressure that produces the flow minus the pressure drop from viscous drag (e.g. Equation 11). $w_0$ is governed by Equation 13. The capacitance is then calculated numerically.

$$C(w_0) = \varepsilon_0 \int_{-a}^{a} \int_{-a}^{a} \frac{dx\,dy}{d - w_0 \cos\left(\frac{\pi x}{2a}\right)\cos\left(\frac{\pi y}{2a}\right)} \quad (15)$$

where d is the capacitor plate spacing in the absence of pressure. The resonant frequency of a closed loop circuit with the sensor in series with an inductance, L, is then:

$$f(w_0) = \frac{1}{2\pi\sqrt{LC(w_0)}} \quad (16)$$

In practice, when the capacitor is used to measure flow, $w_0$, is generally comprised of a static pressure component from the fluid that deflects the flexible membrane inward and a component from the flow governed by Eq. 11 that counteracts the static pressure. If the sensor is in the fluid path of a ventriculoperitoneal shunt, the static pressure at the inlet of the shunt is proportional to the CSF pressure that controls the rate of flow through the shunt. There is also a component of hydrostatic pressure that depends on the path of the fluid, any devices in the path of the fluid (e.g., valves) and the orientation of the shunt with respect to gravity. A single capacitive pressure sensor detects the combined affect of CSF pressure, hydrostatic pressure and flow. The flow component is most conveniently separated by comparing the measurements from two capacitive sensors in the fluid path of the shunt and using Equation 11.

There is no analytical solution for the flow rate as a function of frequency for the case of a square membrane, but by inspection of Eqs. 11, 13, 15, and 16, a non-linear relationship is expected. However, a calibration can be easily recorded. For membrane deflections that are small compared to the gap between the capacitor plates, the theory predicts that the frequency is almost a linear function of the flow rate. For larger deflections the frequency is a non-linear function. The design of the capacitor then dictates the response.

Figure 15:
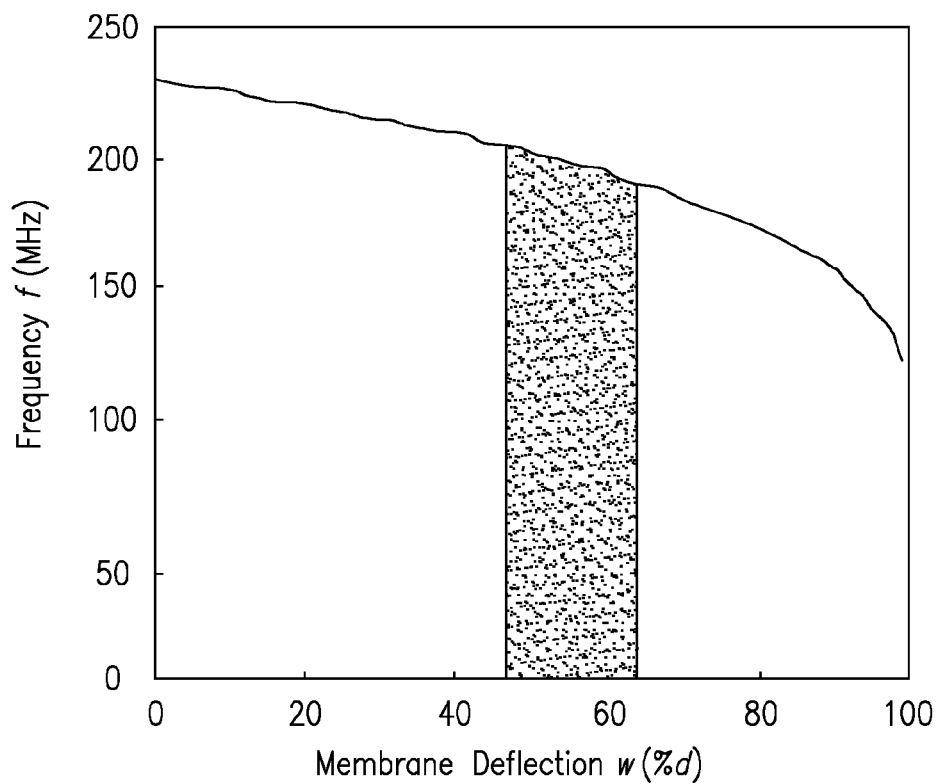
FIG. 15 is a graphical depiction of calculated frequency vs. membrane deflection (plotted as percent of the gap between capacitor plates) for parameters used in accordance with one or more embodiments of the present invention, wherein the shaded area represents the calculated range of deflection for $1<\dot{V}<100$ ml/hr.

As an example, with reference to FIG. 15, the frequency as a function of membrane deflection for a capacitor with the dimensions used for exemplary embodiments herein (a=260 µm and d=0.5 µm) is depicted with L=0.08 µH. Highlighted in FIG. 15 is the approximate range of membrane deflections that would be expected for a sensor that is 20 cm from the inlet of the shunt with D=0.8 mm, t=0.5 µm and $\sigma_0$=250 MPa and an inlet pressure of 1960 Pa (47%<$w_0$<63% of d). The frequency is almost linear within this relatively small range deflection/pressure. For a clinical implementation, the outlet of the shunt is in the peritoneal cavity and the pressure needed to generate flow under such conditions should be taken into account. A reference pressure (atmospheric) was used in experiments disclosed herein, however, the twin capacitor case is described as in connection with a preferred method for an implanted system.

Experiments
Materials and Methods
Capacitive Sensor Fabrication

Figure 16:
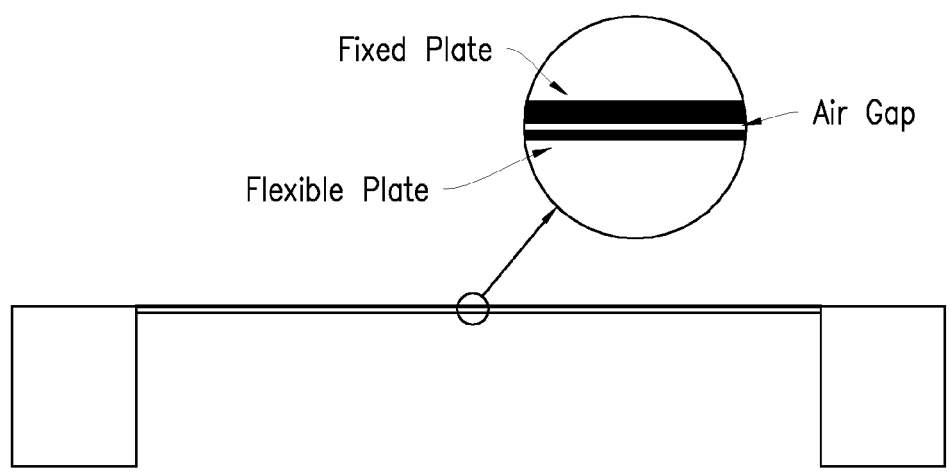
FIG. 16 depicts a schematic cross section of a capacitive pressure sensor in accordance with one or more embodiments of the present invention, wherein the air gap is vented to atmospheric pressure.

Pressure-sensitive capacitors were fabricated using MEMS technology. The core of the sensor is the capacitor with a flexible membrane. With reference to FIG. 16, an example of a capacitor (approximately to scale) is shown wherein the capacitor is square with a width, 2a, on a side of 520 µm. The spacing, d, between the fixed and flexible plates is 0.5 µm. The upper thick plate thickness is 1.06 µm and the flexible membrane thickness is 0.55 µm, with uncertainties in all values of <10%. In order to make the capacitor more sensitive, capacitors were fabricated with large edge width to gap ratio 2a/d~1000.

Now referring to FIG. 17, sensors were fabricated from 100 mm silicon wafers 200 (FIG. 17 step a) with a thickness of 400 µm. Layers 230a, 230b of low stress silicon nitride ($SiN_x$) (500 nm), were deposited using low-pressure chemical vapor deposition (LPCVD) on both sides of the wafer 200 (FIG. 17 step b). The bottom electrode 231 (a bi-layer consisting of 10 nm of Cr and 40 nm of Ni) was defined by photolithography and deposited using e-beam evaporation (FIG. 17 steps c-e). Next, 500 nm of low stress $SiN_x$ 232 was deposited on top using plasma enhanced chemical vapor deposition (PECVD) (FIG. 17 step f). Chemical mechanical polishing (CMP) was used to planarize the nitride surface such that 500 nm of nitride was left on top of the metal (FIG. 17 step g). Using reactive ion etching (RIE), a window 233 for the capacitor gaps was opened (FIG. 17 steps h and i), followed by deposition of layer 240 of 750 nm of $SiO_2$ using PECVD (FIG. 17 step j). Next CMP was used to polish the $SiO_2$ layer 240 down to a thickness of 500 nm on top of the metal electrode 231 (FIG. 17 step k), defining the capacitor gap. Next, photolithography and e-beam evaporation of Cr (~10 nm), and Ni (~40 nm) and Cr (~10 nm) were used to define the top electrode 235 (FIG. 17 steps l-n). The top electrode 235 was patterned such that 5 micron width slots were opened to the $SiO_2$ layer, which is later used for the sacrificial etch. 1 µm of low stress $SiN_x$ 236 was deposited using PECVD to protect the devices (FIG. 17 step o). Windows 241 in the $SiN_x$ for both the contacts and the sacrificial etch were opened using photolithography and RIE (FIG. 17 steps p and q). Next, photolithography using backside alignment and RIE was used to open windows 239 in the nitride layer 230b on the back side of the wafer 200 (FIG. 17 steps r and s). This patterned nitride layer 230b is a hard mask for the through wafer etch. The silicon wafer 200 was anisotropically etched through the wafer using KOH (FIG. 17 step t). A thin layer of ProTEK (from Brewer Science, Inc) was spun on the front side of the wafer 200 and the wafer was mounted in a custom built holder to protect it during the KOH etch. The sacrificial $SiO_2$ layer 240 was etched by dipping the wafer in hydrofluoric acid (HF) acid (FIG. 17 step u). Finally, the wafer 200 was diced and the final device dimensions were 10 mm×5 mm×0.4 mm. With these conditions, the capacitance, $C=4\varepsilon_0 a^2/d$, at the pressure P=0 is 4.8 pF.

In accordance with another example, a dual layer differential flow sensor may be fabricated employing $Al_2O_3$ as an oxide etch barrier. With reference to FIG. 18A, a structure was fabricated as follows: 1 µm layers 210, 220 of $SiO_2$ were deposited using LPCVD on each of the bottom and top surfaces of an undoped Si wafer 200. A first layer 260 of $Al_2O_3$ (20 nm) was deposited on the top $SiO_2$ layer 220 using ALD. A 500 nm layer of low stress $SiN_x$ 230 was deposited on the first layer 260 of $Al_2O_3$ using PECVD. A second layer 262 of $Al_2O_3$ (20 nm) was deposited on the SiNx layer 230 using ALD. A 500 nm layer of $SiO_2$ 240 was deposited on the second layer of $Al_2O_3$ 262 using PECVD. Photolithography was performed using a metal mask, reactive ion etch was applied, with the etch stopping at the second $Al_2O_3$ layer 262. A 700 nm Ti layer 250 was deposited conformally using sputtering.

Now referring to FIG. 18B, chemical-mechanical planarization (CMP) was performed on the Ti layer 250, stopping on the oxide. A third layer 264 of $Al_2O_3$ (20 nm) was deposited on the planarized surface. A second layer 232 of low stress SiNx (200 nm) was deposited on the third $Al_2O_3$ layer 264. Photolithography using a window mask was performed, etching the second $SiN_x$ layer 232, stopping at the third $Al_2O_3$ layer 264. The resist was stripped in a downstream asher. Photolithography using a contact mask was performed using reactive ion etching of a region of the third $Al_2O_3$ layer 264, stopping at the Ti layer 250. The resist was stripped in a downstream asher.

Figure 18C:
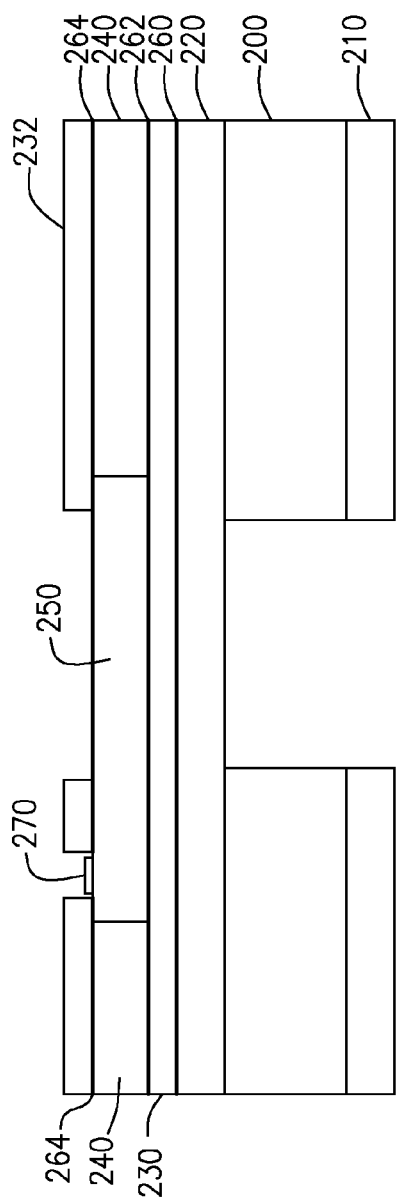

Now referring to FIG. 18C, a 1.1 μm layer of SiO2 was deposited on the bottom $SiO_2$ layer to thicken the layer to 2.1 μm. Photolithography was performed using a contact mask, and a 250 nm gold layer 270 was deposited on the Ti layer 250 in the region in which the third $Al_2O_3$ layer 264 was etched. The photoresist was removed and subsequent photolithography was performed on the bottom $SiO_2$ layer 210, etching the $SiO_2$ layer 210 and stopping at the bottom surface of the Si wafer 200. The resist was stripped in a downstream asher. Further photolithography was applied to the bottom surface of the structure employing a mask on the bottom side. SPR-220-7 photoresist was spun on the top surface to protect the top surface of the structure. The structure was baked at 90° C. for 24 hrs. The exposed Si wafer 200 was then Bosch etched, stopping at the bottom of the top $SiO_2$ layer 220.

Figure 18D:
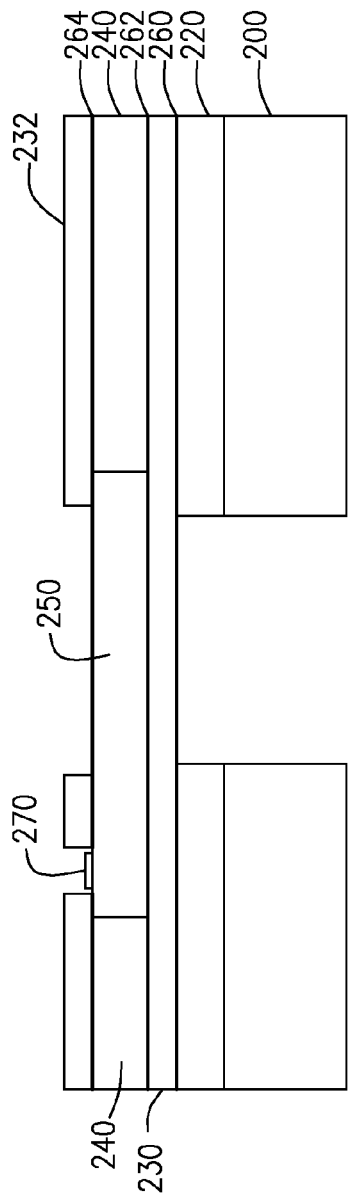

Now referring to FIG. 18D, top $SiO_2$ layer 220 was etched, stopping at the bottom of the first $Al_2O_3$ layer 260. The structure was diced and the resist was stripped in acetone/IPA.

The foregoing examples are illustrative. It will be apparent to those skilled in the art that sensors in accordance with the present disclosure may be fabricated according to a number of different schemes, using various acceptable materials and designs.

Incorporation of Inductor Coil and Chip Carrier with the Chip

In one embodiment a chip carrier may be a rectangular piece of biocompatible material (such as medical grade plexiglass), which serves as a platform that can accommodate the variable capacitor chip. For example, a chip carrier may be a cubic block of 1.3×0.9×0.2 cm with a fluid channel of 0.8 mm diameter that is planar and runs straight through the carrier allowing the fluid to enter at one end and exit through the other. This configuration allows the fluid to make contact with the lower part of the capacitors when the chip is placed on top of the chip carrier. The capacitor chip is glued to the top of the carrier to form a watertight seal. Next, inductors were coupled to each of the pressure sensors by directly soldering the inductor coils onto the capacitor plate leads.

Test Configuration

Figure 19:
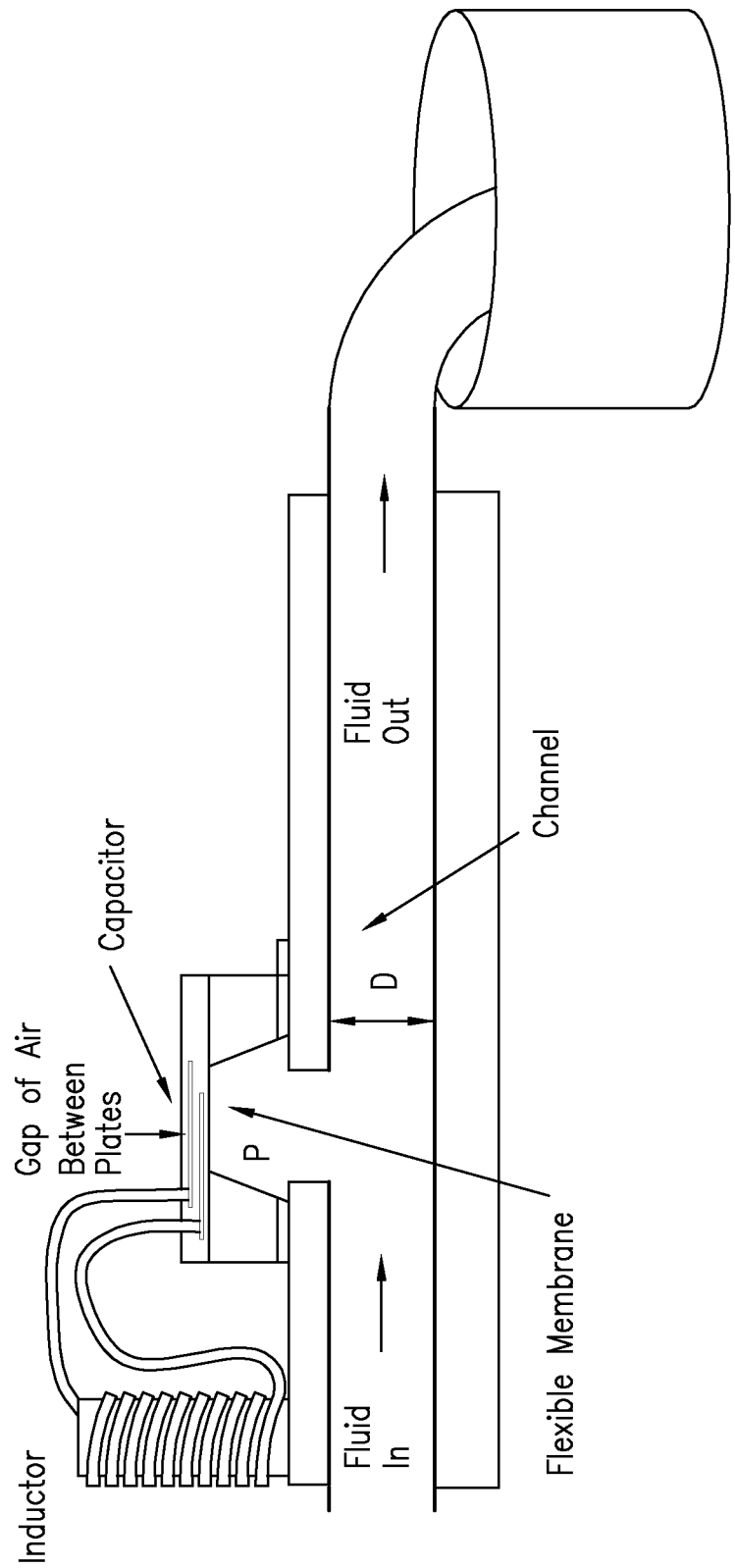
FIG. 19 depicts a schematic, cross-sectional view of a test configuration for a single sensor in accordance with one or more aspects of the present invention.

The configuration of the sensor used for the tests reported here is shown in FIG. 19. Fluid flows such as for example from a computer-controlled syringe pump through a channel of width D=0.8 mm to a collector at atmospheric pressure which serves as a reference. The gap between the plates is vented, such that the air in between is also at atmospheric pressure. A distance l=10 cm separates the sensor from the reference. An important feature of the design is that the entire fluid path, including the channel has a width greater or equal to 0.8 mm (the standard shunt tube inner diameter). There is no flow obstruction, but flow through the fluid resistance along the path produces a pressure difference, which allows the flow measurement.

Examples of the sensors and the spectrometer are shown in FIGS. 20a and 20b. FIG. 20a depicts photographs of test sensors with a single capacitor (top) a twin-capacitor sensor (bottom). FIG. 20b depicts a flow control unit (syringe pump) and spectrometer (resonance frequency reader) with a test sensor on a chip carrier. The fluid used for testing was deionized (DI) water. The spectrometer was a custom-built, frequency synthesizer that sweeps a variable frequency signal to excite the detector coil.

With reference to FIG. 20c an experimental set-up for testing a sensor is shown. Here the pressure difference between the reference (beaker) and the flow sensor is produced by the flow in a shunt tube of known flow resistance R. The change in resonant frequency is read wirelessly by the spectrometer (reader) as the rate of flow is controlled by the syringe pump.

Clinical Configuration

Figure 21:
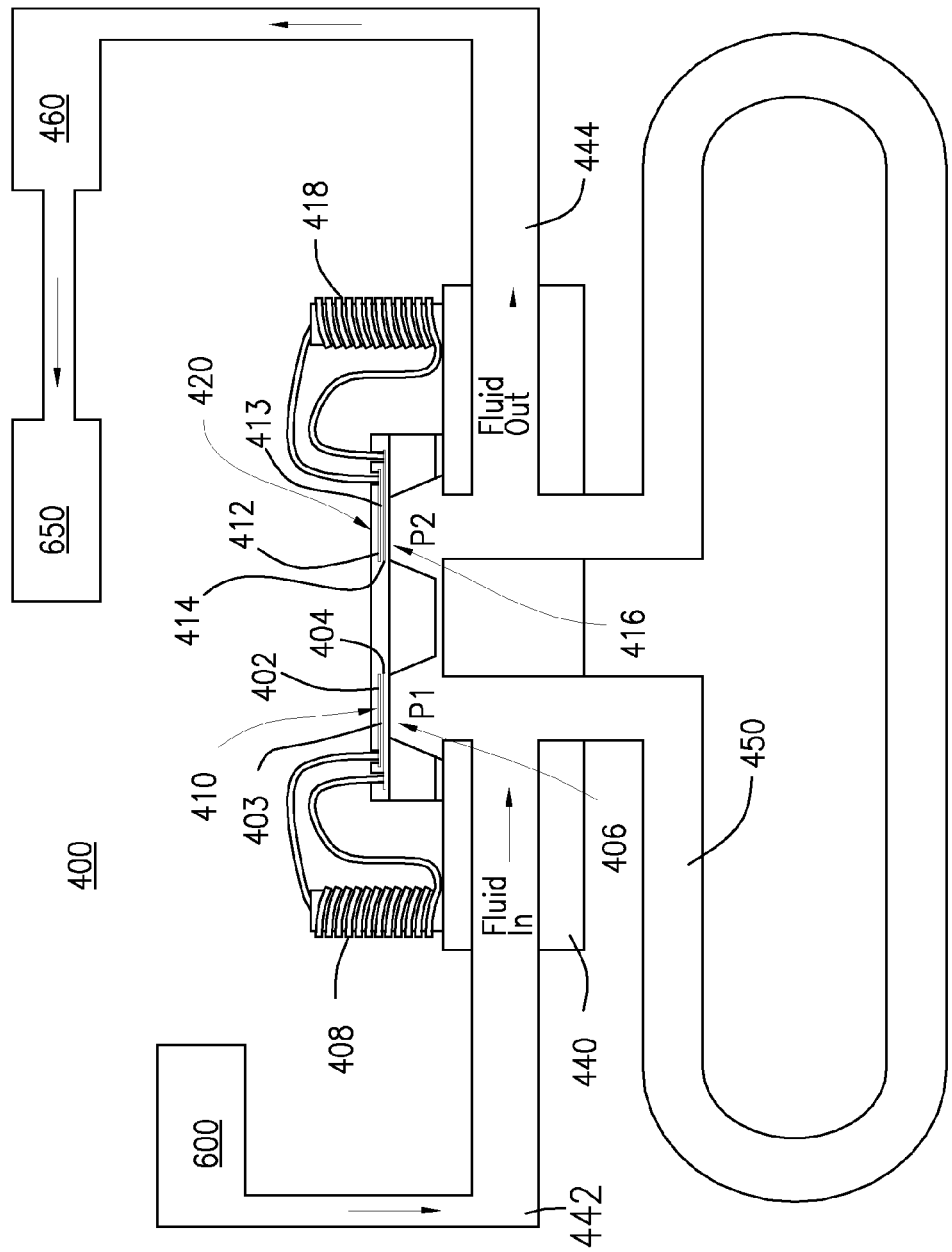
FIG. 21 depicts a schematic, cross-sectional view of a clinical configuration for a flow/pressure sensor in accordance with one or more aspects of the present invention.

Now referring to FIG. 21, a clinical configuration of a dual-capacitor flow/pressure sensor system 400 in accordance with the present disclosure is shown. Sensor system 400 includes sensors 410 and 420 operably linked with a ventricular-peritoneal shunt 440 and a pressure control device 460. Sensor 410 includes top capacitor plate 402 and bottom capacitor plate 404 with air gap 403 disposed therebetween and membrane 406 disposed on a side of the bottom capacitor plate 404 opposite the air gap 403. Sensor 420 includes top capacitor plate 412 and bottom capacitor plate 414 and air gap 413 disposed therebetween and membrane 416 disposed on a side of the bottom capacitor plate 414 opposite the air gap 413. Inductors 408 and 418 are operably connected to capacitors 410 and 420, respectively.

With the expectation of a variable pressure in the brain and the peritoneal cavity and a variable flow resistance in the pressure control valve, there is no reference pressure accessible except in the gap of the capacitor. The solution is to employ dual capacitors and use the difference signal as a measure of flow and the average as a measure of pressure. A tilt-sensor (not shown) may also be used to improve accuracy.

Fluid flows from the ventricle 600 through a ventricular catheter 442 of shunt 440 to the first sensor 410, which measures P1 relative to the gas encapsulated between the capacitor plates 402, 404. Fluid then flows through a calibrated length of shunt tube 450 (length of order 10 cm and flow resistance $R_{hyd}$) to the second sensor 420, which measures P2. P2 is lower because of the flow by an amount $P1-P2=R_{hyd} \dot{V}$. When the sensor system 400 is horizontal, the pressure difference and the calibrated value of $R_{hyd}$ determines $\dot{V}$. The average of P1 and P2 determines the pressure P, which is related to the CSF pressure, but must be corrected for the fluid path length from the entrance of the shunt 440 (in the ventricle 600) and the vertical height difference.

When the patient is in the horizontal position, the pressure difference P1–P2 is from the flow. The situation is different when the patient and whole shunt system 400 including the capacitors is in the vertical position. In this case, there is a gravitational, hydrostatic pressure difference across the 1.5 mm height between the two sensors 410, 420, with the standard formula $P2-P1=\rho gh$, where ρ is the density of the fluid, g is the gravitational constant and h is the height of fluid, and pressure is often given in terms of h in units of mm $H_2O$. Even for h=1.5 mm $H_2O$, the pressure needs to be included in the analysis, but it is known and it is constant. A tilt sensor may be useful to improve the accuracy.

After the fluid passes both sensors 410, 420, the fluid proceeds through tube 444 to a conventional pressure control device 460, of which there are various successful examples commercially available. The pressure control device 460 substantially modifies the relationship between flow and pressure and the variations in this relationship makes a device that measures both P and F more valuable. Now referring to FIG. 22, flow as a function of pressure for three different commercially available control valves used in commercial ventriculo-peritoneal shunts is shown. All of the referenced valves close when the patient is supine, which corresponds to negative pressures on the x-axis of FIG. 22. The control valves are always set to open only at a positive pressure. Therefore, when the valves are set properly to avoid back flow, zero flow will be available as a reference condition. In other conditions, when the valve is open, flows will be reduced by the valve, but still measurable.

Method for Obtaining Pressure and Flow Information Using Twin Sensors and Patient's Position As shown in FIG. 21, in a smart shunt system in accordance with the present disclosure, the flow originates in the ventricle, goes through a tube 442 to the first sensor 410, then the second sensor 420, then through a tube 444 to a pressure control valve 460 and finally to the peritoneal cavity 650. With this set of components and the use of two patient positions, the set of measurements can determine both the ventricle pressure and the flow.

Figure 23:
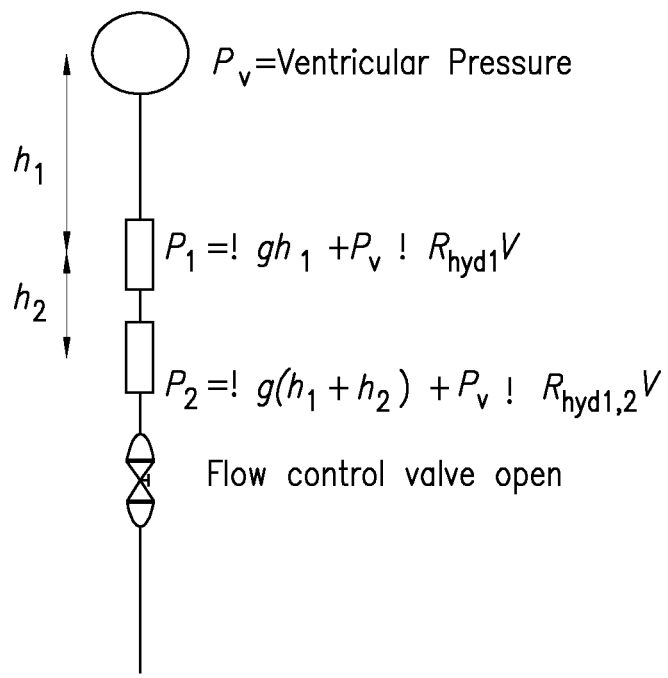
FIG. 23 is a schematic diagram of a method for measuring pressure and flow in a shunt in accordance with one or more aspects of the present invention.
Figure 23:
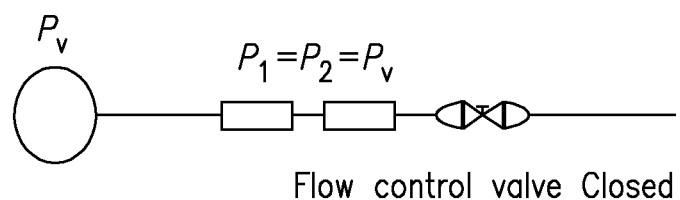

Now referring to FIG. 23, a method for measuring pressure and flow in a shunt in accordance with the present disclosure is shown. With the shunt vertical, the differential pressure $\Delta P = P_1 - P_2$ would determine the flow, $\dot{V}$, corrected by the hydrostatic pressure calculated from the height, $h_2$. When the shunt is horizontal the flow is zero and the ventricular pressure, $P_V$, would be determined by the value of either of the pressure sensors.

Supine Patient Position

Figure 22:
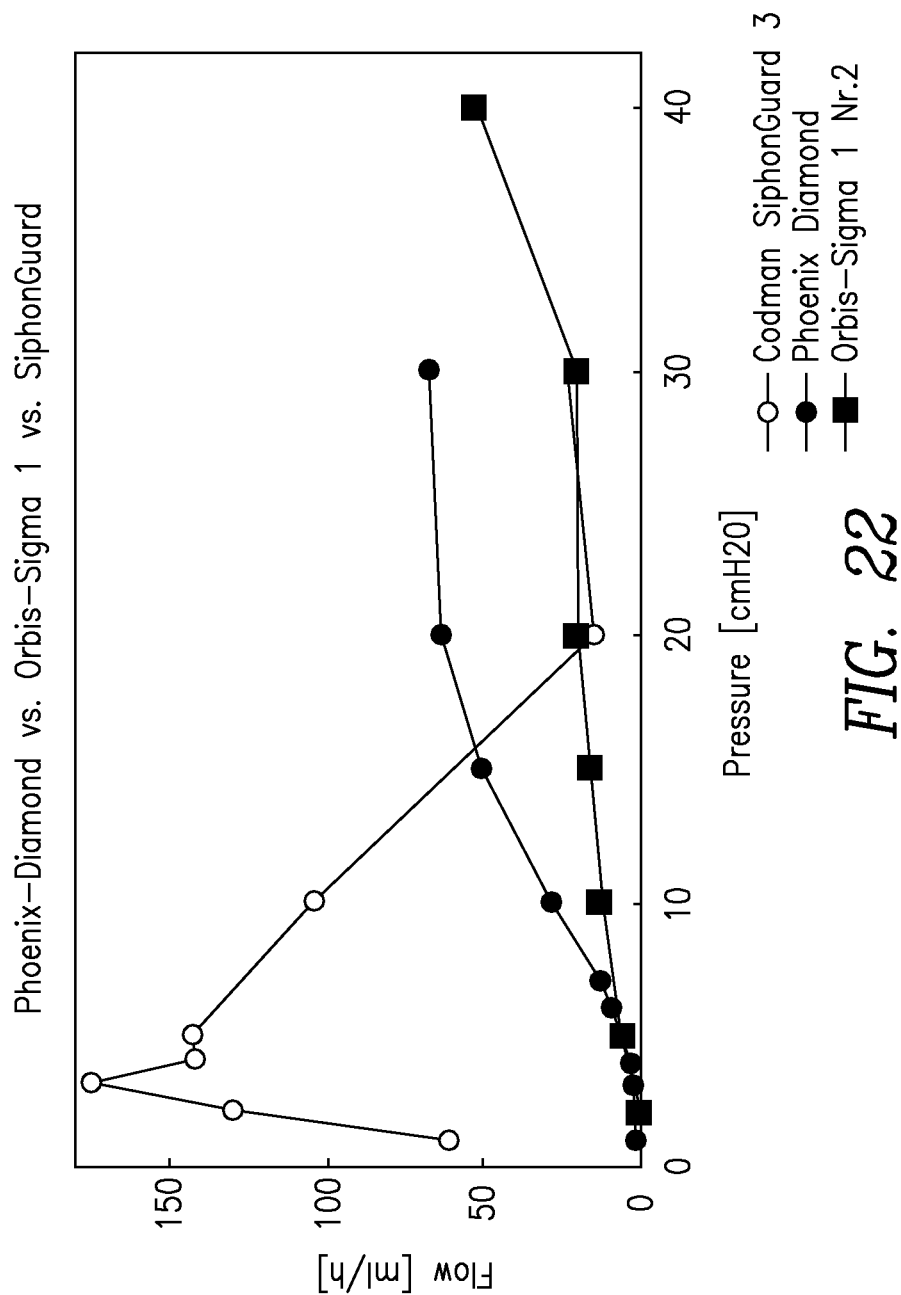
FIG. 22 is a graphical depiction of flow vs. pressure for three control valves used in commercial ventriculo-peritoneal shunts.

All of the valves measured in FIG. 22 cut off the flow when the patient is supine in order to prevent back flow. In this condition, the difference pressure between sensors 410, 420 can be calibrated because the flow is 0. The pressure measured by our implanted sensors is indicative of the pressure in the brain, assuming the end of the shunt tube in the ventricle is horizontal with sensor.

Vertical Patient Position

All of the valves measured in FIG. 22 open at some value of pressure when the patient is vertical. They restrict the flow to avoid draining the ventricle. A relatively large pressure will be measured at a value due to intracranial pressure plus the hydrostatic pressure between the (known) height of the ventricular end of the shunt tube and the sensor. Also, at the first sensor in line with the flow, the pressure will be reduced by the hydraulic flow resistance along the path from the end of the shunt tube in the ventricle, $R_{hyd1}$. In the vertical position, the sensors of FIG. 21 show an internal hydrostatic offset which is significant, but known, so that the flow can be calculated by measuring the pressure difference between the two sensors 410, 420 (i.e., Equations 11 and 12).

Occlusion

One of the most important conditions of the shunt is a malfunction because of an occlusion. Although it may be possible to gain some information from the pressure measurements, the combination of pressure and flow will be most valuable. For example, with a vertical patient, a history of flow readings may be recorded over time. A systematic decrease in the flow rate for a vertical patient may indicate a narrowing of the flow path between the ventricle and any point in the shunt tube. A stoppage of flow indicates an occlusion. In this case, the pressure will only be due to the height difference in the shunt tube. Further confirmation is that, with the patient horizontal, the ventricular pressure will result from the sensor pressure reading. Measurements presented below indicate the characteristics of this type of system.

Results and Discussion

Frequency Vs. Flow Rate

Figure 24:
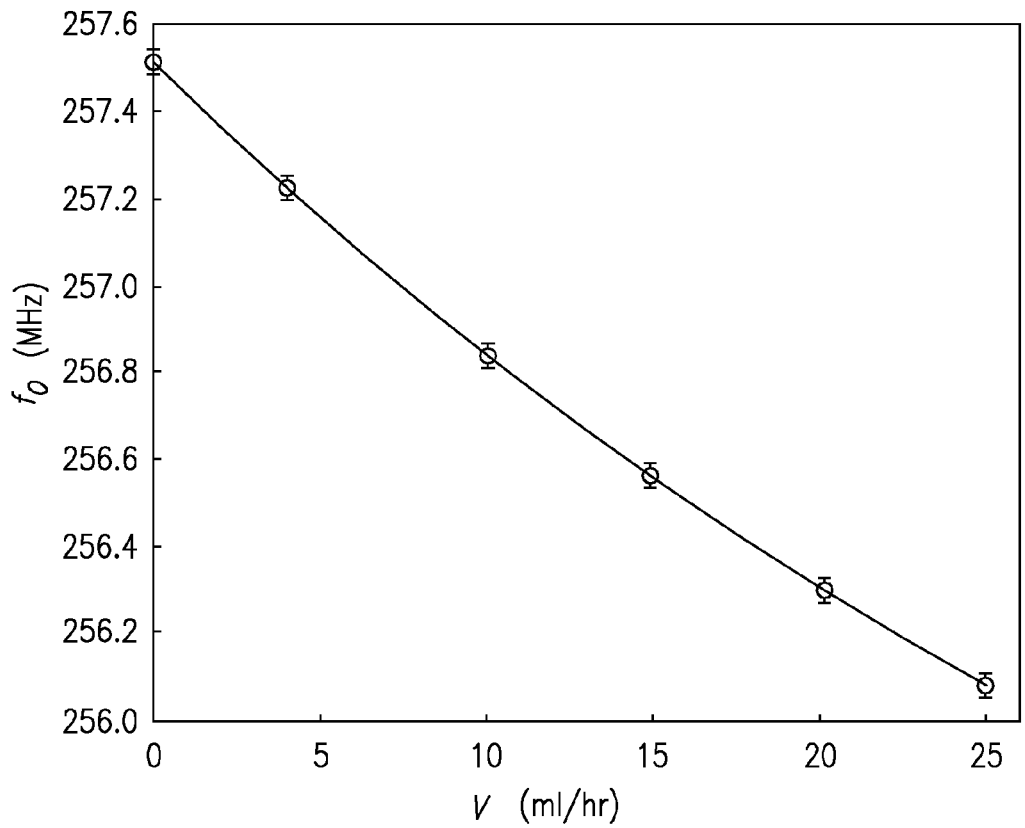
FIG. 24 is a graphical depiction of pressure sensor evaluation tests indicating basic response to controlled flow in accordance with one or more aspects of the present invention; the units of 10 mL/hr correspond to 2.8 μl/s.

The frequency variation as a function of flow rate measured using the configuration shown in FIG. 20 is shown in FIG. 24. These data show a quadratic relation between resonant frequency, $f_0$, and flow rate, $\dot{V}$, of $f_0 = m_1 \dot{V} + m_2 \dot{V}^2 + b$, where $m_1 = -72$ (kHz-hr/ml), $m_2 = 0.648$ (kHz-(hr/mL)$^2$) and b=257.5 MHz over a flow range up to 25 mL/hr or (10 µL/s). The uncertainty in measuring the resonant frequencies is 30 kHz, as indicated by the error bars, with this small value arising because we fit the data delineating the resonance and extract the center frequency from the fit. The fit provides a statistically accurate description of the data with $R^2 = 0.9992$. The uncertainty in the linear part of the slope, $m_1 = 3$ and in the quadratic part, $m_2 = 0.1$, both small values because of the accuracy in $f_0$ and $\dot{V}$. In this case the maximum deflection of the capacitor membrane predicted from theory (Eqs. 11 and 13) is in the range where we would expect a linear response or a slight curve downwards with increasing frequency ($m_2 < 0$). This may be an indication that the model for the shape of the membrane under pressure (Eq. 14) may not be the best representation at small pressures. Also, compliances of the tubing used may introduce an error and settling times at low flows may need to be studied. However, these effects may also be present in clinical use, which further indicates the importance of calibration. The ability of the single capacitor system to resolve different flow values is ~0.6 mL/hr and the sensitivity is of the same order. For the dual capacitor case the sensitivity is proportional to the length of the channel between the two capacitors. It improves linearly with the channel length. In the system of FIG. 20 there is ~60 cm from the single capacitor pressure sensor to the output port, which controls the sensitivity.

Measurements of the same device over a month resulted in a frequency drift equivalent to <0.3 mL/hr, which is on the order of the uncertainty in the flow rate. Systematic drifts in the system are apparently small. Also, the sensitivity to temperature was measured to be equivalent to $\Delta\dot{V} \sim 1$ ml/(hr° C.). It is expected that ambient pressure effects on the sensor in vivo, will be minimal when differential pressure measurements are employed.

Frequency Vs. Pressure

Figure 25:
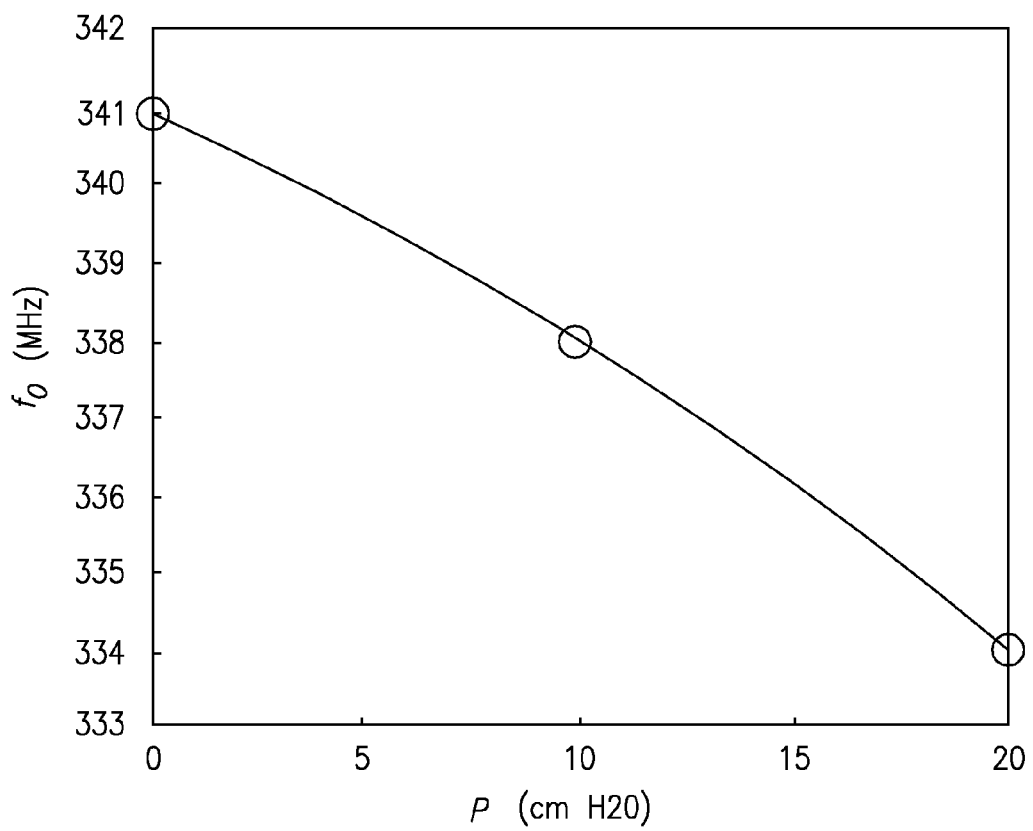
FIG. 25 is a graphical depiction of resonant frequency as a function of the height of a column of water above a pressure-sensitive capacitive sensor in accordance with one or more aspects of the present invention.

The frequency variation as a function of hydrostatic pressure was measured using the configuration shown in FIG. 20 except for the replacement of the syringe pump by a column of water. With reference to FIG. 25, the results show that the resonant frequency, $f_0$, varies quadratically with h as $f_0 = m_1 h + m_2 h^2 + b$, where $m_1 = -0.25$ MHz/cm, $m_2 = -0.005$ (MHz/cm)$^2$. The quadratic term is negative in this case where there is no flow (compare to FIG. 24). This trend is consistent with the prediction of the theory for larger deflections of the membrane and indicates that Eq. 14 is a reasonable representation of the membrane shape at large deflections. The uncertainty in frequency is not shown in the graph because it is small. The uncertainty in h is ~0.01 cm. For the clinical case the expected uncertainty in h is also small because of manufacturing tolerances. An electronic tilt sensor may be employed to compensate for the orientation of the patient.

As discussed earlier the vertical sensor orientation is preferred for twin capacitors in vivo since the shunt valve is open and the hydrostatic pressures can be easily compensated. The degree of verticality is important. As an example for the sensors that we have tested the frequency shift for a hydrostatic pressure corresponding to a sensor height difference of h=1.50 mm is 400 kHz. To reduce the uncertainty, this contribution should be measured carefully. The solution is to have the axis connecting the center of the two capacitors held vertically. In this orientation, the static gravitational pressure difference between the sensors is at a maximum, but it is insensitive to the angle from the vertical. Provided that this contribution remains a constant, a correction can be made because all of the physical parameters are known or can be easily measured. The vertical position is where the shunt valve is open and is also where the difference height as a function of angle, q, from vertical is least sensitive. Also, $$h = h_0 \cos(q), \tag{17}$$

wherein h is slowly varying for q near 0. Tilt sensors are commercially available with sensitivities of 0.01° and with double axes. For the present systems, in one embodiment the height, h=1.50 mm, the fluid density, $\rho=1.007$ gm/cm$^2$, and the gravitational constant, g=980 cm/s$^2$, a tilt angle of 0.01° corresponds to a change in height of only 8/10000 mm. This procedure is feasible even on a capacitor pair that is implanted in a patient. The tilt sensor can be mounted on the external spectrometer. With this control, the value of h can be adjusted to $h_0$ or a correction can be introduced for a finite value of h. The patient can also be moved slightly to maximize the frequency. The twin capacitor system is preferable.

Additional Flow Sensor Evaluation Tests

All of the tests above were carried out wirelessly, using inductive coupling between loops on the sensor and on the reader.

Figure 26A:
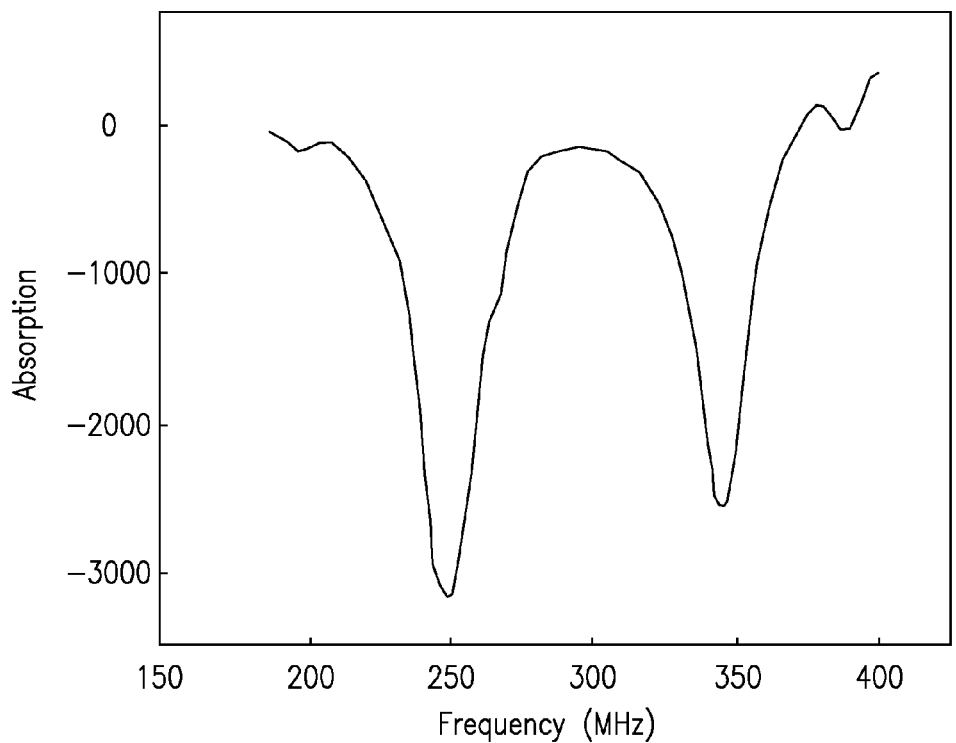
FIG. 26a is a graphical depiction of absorption as a function of frequency in accordance with one or more aspects of the present invention.

Dual Resonance Test:

In a separate test, two different coils for two capacitors were used to produce resonances near 250 MHz and 350 MHz. The data shown in FIG. 26a indicates that the sensor can read two resonances simultaneously.

Figure 26B:
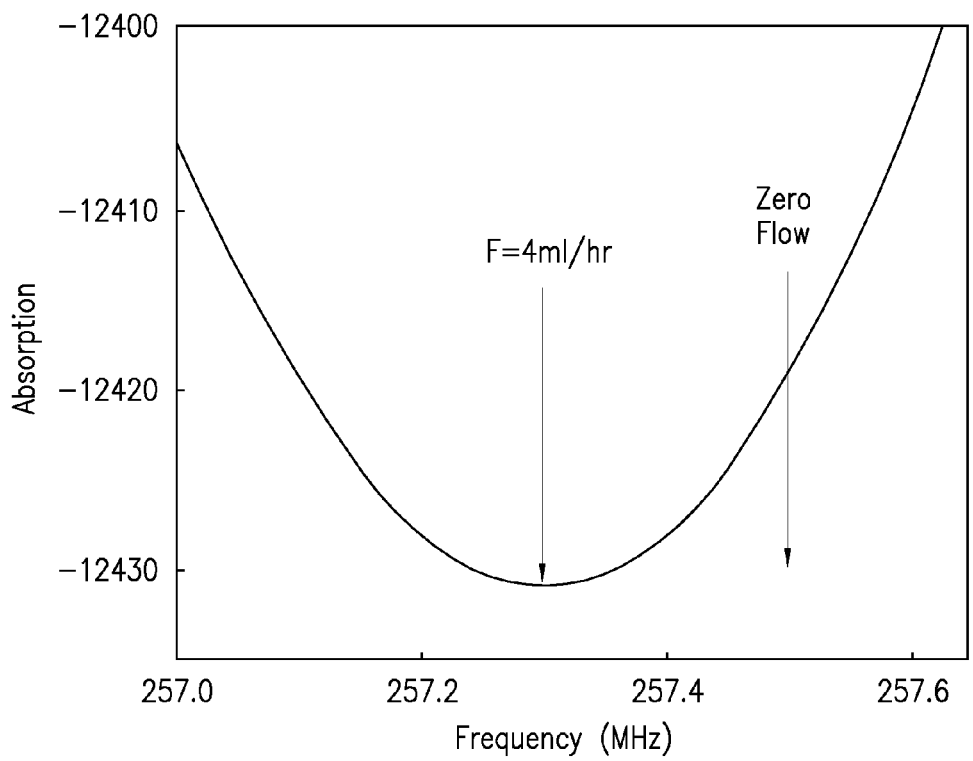
FIG. 26b is a graphical depiction of absorption as a function of frequency near the minimum in accordance with one or more aspects of the present invention.

Sensitivity and Resonance Width Test:

The resonant center frequency can be determined by fitting the entire curve to an uncertainty of 30 kHz much less than the resonance width, as shown in FIG. 26b. In the two measurements noted here, the resonance shift was 200 kHz with a standard deviation of 30 kHz was determined between zero flow and 4 mL/hr.

As noted above, sensors as disclosed herein coupled to standard shunts may be measured with an external wireless spectrometer and an orientation sensor. Test results from a MEMS-based capacitive pressure sensor show that systems disclosed herein may be sensitive to flow rates from below 0.6 mL/hr to above 100 mL/hr. Such systems are also sensitive to pressures from less than 1 mm H$_2$O to more than 200 mm H$_2$O.

Devices and methods in accordance with the present disclosure are operable to head off brain injury and death, reduce brain surgeries and test medicines.

Although the systems and methods of the present disclosure have been described with reference to exemplary embodiments thereof, the present disclosure is not limited thereby. Indeed, the exemplary embodiments are implementations of the disclosed systems and methods are provided for illustrative and non-limitative purposes. Changes, modifications, enhancements and/or refinements to the disclosed systems and methods may be made without departing from the spirit or scope of the present disclosure. Accordingly, such changes, modifications, enhancements and/or refinements are encompassed within the scope of the present invention.

REFERENCES

All references listed are incorporated herein by reference in their entirety.

Di Rocco, C., L. Massimi, and G. Tamburrini, Shunts vs endoscopic third ventriculostomy in infants: are there different types and/or rates of complications? A review. Childs Nerv Syst, 2006. 22(12): p. 1573-89.

Garton, H. J. and J. H. Piatt, Jr., Hydrocephalus. Pediatr Clin North Am, 2004. 51(2): p. 305-25.

Robertson, J. S., M. I. Maraqa, and B. Jennett, Ventriculoperitoneal shunting for hydrocephalus. British medical journal, 1973. 2(5861): p. 289-292.

Vinchon, M., et al., Shunt revision for asymptomatic failure: surgical and clinical results. Neurosurgery, 2003. 52(2): p. 347-53; discussion 353-6.

Caldarelli, M., C. Di Rocco, and F. La Marca, Shunt complications in the first postoperative year in children with meningomyelocele. Childs Nerv Syst, 1996. 12(12): p. 748-54.

Blount, J. P., J. A. Campbell, and S. J. Haines, Complications in ventricular cerebrospinal fluid shunting. Neurosurg Clin N Am, 1993. 4(4): p. 633-56.

Kulkarni, A. V., et al., Predicting who will benefit from endoscopic third ventriculostomy compared with shunt insertion in childhood hydrocephalus using the ETV Success Score. Journal of Neurosurgery: Pediatrics, 2010. 6(4): p. 310-315.

Kulkarni, A. V., et al., Endoscopic Third Ventriculostomy Vs Cerebrospinal Fluid Shunt in the Treatment of Hydrocephalus in Children: A Propensity Score-Adjusted Analysis. Neurosurgery, 2010. 67(3): p. 588-593 10.1227/01.NEU.0000373199.79462.21.

Sekula, R. F., et al., Laparoscopically assisted peritoneal shunt insertion for hydrocephalus. British Journal of Neurosurgery, 2009. 23(4): p. 439-442.

Winston, K. R., J. A. Lopez, and J. Freeman, CSF Shunt Failure with Stable Normal Ventricular Size. Pediatric Neurosurgery, 2006. 42(3): p. 151-155.

Akar, O., T. Akin, and K. Najafi, A wireless batch sealed absolute capacitive pressure sensor. Sensors and Actuators A: Physical, 2001. 95(1): p. 29-38.

Chang, S.-P. and M. G. Allen, Demonstration for integrating capacitive pressure sensors with read-out circuitry on stainless steel substrate. Sensors and Actuators A: Physical, 2004. 116(2): p. 195-204.

Lei, K. F., K.-F. Lee, and M.-Y. Lee, Development of a flexible PDMS capacitive pressure sensor for plantar pressure measurement. Microelectronic Engineering, 2012. 99(O): p. 1-5. Ha, D., et al., Polymer-based miniature flexible capacitive pressure sensor for intraocular pressure (IOP) monitoring inside a mouse eye. Biomedical Microdevices, 2012. 14(1): p. 207-215.

Sutera, S. P. and R. Skalak, The History of Poiseuille's Law Annual Review of Fluid Mechanics, 1993. 25(1): p. 1-20.

Oosterbroek, R. E., et al., A micromachined pressure/flow-sensor. Sensors and Actuators A: Physical, 1999. 77(3): p. 167-177.

Oosterbroek, R. E., et al. Designing, realization and characterization of a novel capacitive pressure/flow sensor. in Solid State Sensors and Actuators, 1997. TRANSDUCERS '97 Chicago., 1997 International Conference on. 1997.

Vlassak, J. J. and W. D. Nix, New bulge test technique for the determination of Young's modulus and Poisson's ratio of thin films. Journal of Materials Research, 1992. 7(12): p. 3242-3249.

Pan, J. Y., et al. Verification of FEM analysis of load-deflection methods for measuring mechanical properties of thin films. in Solid-State Sensor and Actuator Workshop, 1990. 4th Technical Digest., IEEE. 1990.

Ohta, T., et al., Development of a Fully Implantable Epidural Pressure (EDP) Sensor, in Intracranial Pressure VII, J. Hoff and A. L. Betz, Editors. 1989, Springer Berlin Heidelberg. p. 48-51. (Reprinted with kind permission from Springer Science and Business Media).

Irani, D. N., Properties and Composition of Normal Cerebrospinal Fluid, in Cerebospinal Fluid In Clinical Practice, D. N. Irani, Editor 2009, Saunders Elsevier: Philadelphia. p. 69.

What is claimed is:

1. A device comprising a micro-electromechanical system (MEMS) sensor having a single capacitor, comprising a rigid capacitor plate and a flexible capacitor plate separated by a distance forming a gap, wherein the flexible capacitor plate is operable to deform in response to pressure exerted by a fluid, wherein the capacitor plates are coupled to an inductor forming a capacitor-inductor loop, wherein the device is operable to convert deformation of the flexible capacitor plate into a change in a resonant absorption of the capacitor-inductor loop.

2. The device according to claim 1 further comprising an external circuit operable to induce an alternating current in the capacitor-inductor loop and measure the absorption resonance to convert the deformation of the flexible capacitor plate in response to the fluid into a change in capacitance.

3. The device according to claim 1 wherein at least one of the capacitor plates includes a surface at least partially coated with an oil.

4. The device according to claim 1 comprising a vent extending from the gap operable to permit background pressure at the sensor to be cancelled by a differential measurement.

5. The device according to claim 1 comprising a flow sensor comprising a chamber formed between an inlet of the fluid-conveying channel and the flexible capacitor plate, the chamber operable to receive fluid exiting the channel and further comprising an outlet formed in the chamber to permit flow of the fluid out of the chamber, wherein pressure of the fluid in the chamber causes the flexible capacitor plate to deform toward the rigid capacitor plate and thereby reduce the separation between the flexible and rigid capacitor plates and reduce the capacitance relative to the capacitance when no flowing fluid is present.

6. The device according to claim 5 wherein the fluid exits the outlet to a tube with a calibrated flow resistance to contact an opposite side of the flexible capacitor plate, wherein the device measures a pressure difference across the membrane.

7. The device according to claim 1 comprising a pressure sensor further comprising a shunt tube comprising an opening adjacent a chamber formed adjacent the flexible capacitor plate, wherein pressure of the fluid is transmitted through the fluid to the chamber.

8. The device according to claim 7, wherein the gap between the capacitor plates is sealed and comprises a fixed quantity of gas, and wherein a change in pressure of the fluid changes the capacitance and resonant property of the capacitor-inductor loop.

9. The device according to claim 1 coupled to a shunt operable to be implanted in a body of a patient, wherein the flexible capacitor plate is positioned to be in fluid connection with a fluid-conveying channel of the shunt.

10. The device according to claim 9 wherein the shunt is an ocular shunt.

11. The device according to claim 9 further comprising a flow regulation device comprising a valve disposed in the channel of the shunt.

12. A device comprising a micro-electromechanical system (MEMS) sensor having a single capacitor, comprising two flexible capacitor plates separated by a distance forming a gap, wherein the flexible capacitor plates are operable to contact a fluid and deform in response to pressure exerted by the fluid, wherein the flexible capacitor plates are coupled to an inductor forming a capacitor-inductor loop, wherein the device is operable to convert deformation of the flexible capacitor plates into a change in a resonant absorption of the capacitor-inductor loop.

13. The device according to claim 12 wherein the capacitor comprises two chips bonded together, wherein each chip comprises a rigid structure housing a flexible capacitor plate.

14. The device according to claim 12 further comprising an external circuit operable to induce an alternating current in the capacitor-inductor loop and measure the absorption resonance to convert the deformation of the flexible capacitor plate in response to the fluid into a change in capacitance.

15. The device according to claim 12 comprising a vent extending from the gap operable to permit background pressure at the sensor to be cancelled by a differential measurement.

* * * * *